US009101382B2

(12) United States Patent
Krolik et al.

(10) Patent No.: US 9,101,382 B2
(45) Date of Patent: Aug. 11, 2015

(54) APPARATUS AND METHODS FOR TREATING OBSTRUCTIONS WITHIN BODY LUMENS

(75) Inventors: Jeffrey A. Krolik, Campbell, CA (US); Juan Domingo, Lathrop, CA (US); Gwendolyn Watanabe, Sunnyvale, CA (US); Ray Betelia, San Jose, CA (US); Lucas Fernandez, Sunnyvale, CA (US)

(73) Assignee: HOTSPUR TECHNOLOGIES, INC., Mountain View, CA (US)

( * ) Notice: Subject to any disclaimer, the term of this patent is extended or adjusted under 35 U.S.C. 154(b) by 0 days.

(21) Appl. No.: 13/216,208

(22) Filed: Aug. 23, 2011

(65) Prior Publication Data

US 2012/0078096 A1    Mar. 29, 2012

Related U.S. Application Data

(63) Continuation-in-part of application No. 12/843,004, filed on Jul. 23, 2010, now Pat. No. 8,945,160, and a continuation-in-part of application No. 12/497,135, filed on Jul. 2, 2009, now Pat. No. 8,043,313.

(Continued)

(51) Int. Cl.
*A61M 25/10* (2013.01)
*A61B 17/22* (2006.01)
(Continued)

(52) U.S. Cl.
CPC ......... *A61B 17/22032* (2013.01); *A61B 17/221* (2013.01); *A61B 17/320725* (2013.01);
(Continued)

(58) Field of Classification Search
CPC ............... A61M 25/1002; A61M 25/0075; A61M 25/10185; A61F 2/985; A61B 17/32075

USPC ................. 623/1.11–1.54; 604/96.01–103.14
See application file for complete search history.

(56) References Cited

U.S. PATENT DOCUMENTS

| 396,754 A | 1/1889 | Mayfield |
| 4,029,104 A | 6/1977 | Kerber |

(Continued)

FOREIGN PATENT DOCUMENTS

| CN | 1917802 A | 2/2007 |
| EP | 0 778 042 A2 | 6/1997 |

(Continued)

OTHER PUBLICATIONS

PCT International Search Report and Written Opinion for PCT/US2010/043165, Applicant: HotSpur Technologies, Inc., Forms PCT/ISA/220, PCT/ISA/210, and PCT/ISA/237: dated Apr. 11, 2011, 17 pages.

(Continued)

*Primary Examiner* — Kathleen Holwerda
(74) *Attorney, Agent, or Firm* — Baker & Hostetler LLP

(57) ABSTRACT

Apparatus and methods are provided for delivering fluid into a body lumen during a medical procedure. A distal end of an apparatus may be introduced into a body lumen, and a valve on the distal end may be opened to deliver fluid through a first lumen into the body lumen, e.g., contrast and/or other diagnostic or therapeutic agents. The valve may be closed, and a procedure may be performed within the body lumen, e.g., using a treatment element carried on the distal end. For example, the treatment element may include a balloon that may be inflated when fluid is delivered through the first lumen with the valve closed. Optionally, a prosthesis, energy source, drug platform, and the like may be carried by the balloon for treating the body lumen. In various embodiments, the valve may be located proximal or distal to the treatment element.

24 Claims, 21 Drawing Sheets

Related U.S. Application Data

(60) Provisional application No. 61/520,927, filed on Jun. 17, 2011, provisional application No. 61/463,537, filed on Feb. 19, 2011, provisional application No. 61/402,166, filed on Aug. 25, 2010, provisional application No. 61/342,755, filed on Apr. 19, 2010, provisional application No. 61/397,854, filed on Jun. 17, 2010, provisional application No. 61/283,035, filed on Nov. 25, 2009, provisional application No. 61/271,627, filed on Jul. 23, 2009, provisional application No. 61/215,732, filed on May 8, 2009, provisional application No. 61/214,667, filed on Apr. 27, 2009, provisional application No. 61/153,620, filed on Feb. 18, 2009.

(51) Int. Cl.
| | |
|---|---|
| *A61M 25/00* | (2006.01) |
| *A61B 17/221* | (2006.01) |
| *A61F 2/958* | (2013.01) |
| *A61M 29/02* | (2006.01) |
| *A61B 17/3205* | (2006.01) |
| *A61B 17/3207* | (2006.01) |

(52) U.S. Cl.
CPC ............ *A61F2/958* (2013.01); *A61M 25/0075* (2013.01); *A61M 25/10* (2013.01); *A61M 25/1002* (2013.01); *A61M 25/1011* (2013.01); *A61M 29/02* (2013.01); *A61B 17/3207* (2013.01); *A61B 17/32056* (2013.01); *A61B 2017/2212* (2013.01); *A61B 2017/2215* (2013.01); *A61B 2017/22034* (2013.01); *A61B 2017/22061* (2013.01); *A61B 2017/22082* (2013.01); *A61B 2017/22084* (2013.01); *A61M 25/0097* (2013.01); *A61M 25/10185* (2013.11); *A61M 2025/0008* (2013.01); *A61M 2025/109* (2013.01); *A61M 2025/1068* (2013.01); *A61M 2025/1077* (2013.01); *A61M 2025/1084* (2013.01); *A61M 2025/1086* (2013.01)

(56) References Cited

U.S. PATENT DOCUMENTS

| | | | |
|---|---|---|---|
| 4,030,503 A | 6/1977 | Clark, III | |
| 4,273,128 A | 6/1981 | Lary | |
| 4,315,512 A | 2/1982 | Fogarty | |
| 4,545,367 A | 10/1985 | Tucci | |
| 4,646,742 A | 3/1987 | Packard | |
| 4,649,922 A | 3/1987 | Wiktor | |
| 4,653,496 A | 3/1987 | Bundy et al. | |
| 4,706,671 A | 11/1987 | Weinrib | |
| 4,762,130 A * | 8/1988 | Fogarty et al. | 606/159 |
| 4,784,636 A | 11/1988 | Rydell | |
| 4,813,934 A | 3/1989 | Engelson et al. | |
| 4,821,722 A | 4/1989 | Miller et al. | |
| 4,848,342 A | 7/1989 | Kaltenbach | |
| 4,848,344 A | 7/1989 | Sos et al. | |
| 4,890,611 A | 1/1990 | Monfort et al. | |
| 4,894,051 A | 1/1990 | Shiber | |
| 4,921,478 A | 5/1990 | Solano et al. | |
| 4,926,858 A | 5/1990 | Gifford, III et al. | |
| 4,950,277 A | 8/1990 | Farr | |
| 5,011,488 A | 4/1991 | Ginsburg | |
| 5,032,113 A | 7/1991 | Burns et al. | |
| 5,035,705 A | 7/1991 | Burns | |
| 5,059,176 A | 10/1991 | Winters | |
| 5,085,636 A | 2/1992 | Burns | |
| 5,090,959 A | 2/1992 | Samson et al. | |
| 5,100,388 A | 3/1992 | Behl et al. | |
| 5,100,423 A | 3/1992 | Fearnot | |
| 5,102,402 A * | 4/1992 | Dror et al. | 604/265 |
| 5,135,494 A | 8/1992 | Engelson | |
| 5,135,531 A | 8/1992 | Shiber | |
| 5,141,518 A | 8/1992 | Hess et al. | |
| 5,171,221 A | 12/1992 | Samson | |
| 5,176,698 A | 1/1993 | Burns et al. | |
| 5,192,286 A | 3/1993 | Phan et al. | |
| 5,192,290 A | 3/1993 | Hilal | |
| 5,192,295 A | 3/1993 | Danforth et al. | |
| 5,207,229 A | 5/1993 | Winters | |
| 5,211,651 A | 5/1993 | Reger et al. | |
| 5,217,434 A | 6/1993 | Arney | |
| 5,221,260 A | 6/1993 | Burns et al. | |
| 5,259,839 A | 11/1993 | Burns | |
| 5,295,959 A | 3/1994 | Gurbel et al. | |
| 5,303,714 A | 4/1994 | Abele et al. | |
| 5,304,198 A | 4/1994 | Samson | |
| 5,308,356 A | 5/1994 | Blackshear et al. | |
| 5,312,340 A | 5/1994 | Keith | |
| 5,320,604 A | 6/1994 | Walker et al. | |
| 5,338,295 A | 8/1994 | Cornelius et al. | |
| 5,342,301 A | 8/1994 | Saab | |
| 5,364,354 A | 11/1994 | Walker et al. | |
| 5,368,567 A | 11/1994 | Lee | |
| 5,372,601 A | 12/1994 | Lary | |
| 5,378,238 A | 1/1995 | Peters et al. | |
| 5,380,282 A | 1/1995 | Burns | |
| 5,383,856 A | 1/1995 | Bersin | |
| 5,385,152 A | 1/1995 | Abele et al. | |
| 5,403,276 A | 4/1995 | Schechter et al. | |
| 5,415,634 A | 5/1995 | Glynn et al. | |
| 5,419,774 A | 5/1995 | Willard et al. | |
| 5,423,745 A | 6/1995 | Todd et al. | |
| 5,423,846 A | 6/1995 | Fischell | |
| 5,437,632 A * | 8/1995 | Engelson | 604/523 |
| 5,454,788 A | 10/1995 | Walker et al. | |
| 5,454,789 A | 10/1995 | Burns et al. | |
| 5,464,395 A | 11/1995 | Faxon et al. | |
| 5,476,477 A | 12/1995 | Burns | |
| 5,484,408 A | 1/1996 | Burns | |
| 5,484,409 A | 1/1996 | Atkinson et al. | |
| 5,484,411 A | 1/1996 | Inderbitzen et al. | |
| 5,487,730 A | 1/1996 | Marcadis et al. | |
| 5,527,326 A | 6/1996 | Hermann et al. | |
| 5,569,195 A | 10/1996 | Saab | |
| 5,569,201 A | 10/1996 | Burns | |
| 5,571,122 A | 11/1996 | Kelly et al. | |
| 5,624,396 A | 4/1997 | McNamara et al. | |
| 5,643,298 A | 7/1997 | Nordgren et al. | |
| 5,643,304 A | 7/1997 | Schechter et al. | |
| 5,658,302 A | 8/1997 | Wicherski et al. | |
| 5,662,603 A | 9/1997 | Gelbfish | |
| 5,665,098 A | 9/1997 | Kelly et al. | |
| 5,683,410 A | 11/1997 | Samson | |
| 5,693,015 A | 12/1997 | Walker et al. | |
| 5,728,067 A | 3/1998 | Enger | |
| 5,749,849 A | 5/1998 | Engelson | |
| 5,766,191 A | 6/1998 | Trerotola | |
| 5,776,099 A | 7/1998 | Tremulis | |
| 5,779,698 A * | 7/1998 | Clayman et al. | 606/39 |
| 5,807,328 A * | 9/1998 | Briscoe | 604/102.02 |
| 5,836,961 A | 11/1998 | Kieturakis et al. | |
| 5,843,103 A | 12/1998 | Wulfman | |
| 5,868,735 A | 2/1999 | Lafontaine | |
| 5,868,768 A | 2/1999 | Wicherski et al. | |
| 5,891,153 A | 4/1999 | Peterson | |
| 5,895,398 A | 4/1999 | Wensel et al. | |
| 5,906,606 A | 5/1999 | Chee et al. | |
| 5,919,162 A | 7/1999 | Burns | |
| 5,947,985 A | 9/1999 | Imran | |
| 5,954,737 A | 9/1999 | Lee | |
| 5,972,019 A | 10/1999 | Engelson et al. | |
| 5,980,486 A | 11/1999 | Enger | |
| 5,997,557 A | 12/1999 | Barbut et al. | |
| 6,004,328 A | 12/1999 | Solar | |
| 6,017,323 A * | 1/2000 | Chee | 604/96.01 |
| 6,036,717 A | 3/2000 | Mers et al. | |
| 6,050,972 A | 4/2000 | Zadno-Azizi et al. | |
| 6,066,158 A | 5/2000 | Engelson et al. | |
| 6,090,126 A | 7/2000 | Burns | |

(56) References Cited

U.S. PATENT DOCUMENTS

| | | |
|---|---|---|
| 6,096,055 A | 8/2000 | Samson |
| 6,113,579 A | 9/2000 | Eidenschink et al. |
| 6,129,708 A | 10/2000 | Enger |
| 6,146,396 A | 11/2000 | Konya et al. |
| 6,210,370 B1 | 4/2001 | Chi-Sing et al. |
| 6,231,543 B1 | 5/2001 | Hegde et al. |
| 6,231,588 B1 | 5/2001 | Zadno-Azizi |
| 6,245,040 B1 | 6/2001 | Inderbitzen et al. |
| 6,283,950 B1 | 9/2001 | Appling |
| 6,306,124 B1 | 10/2001 | Jones et al. |
| 6,306,151 B1 | 10/2001 | Lary |
| 6,325,778 B1 * | 12/2001 | Zadno-Azizi et al. ..... 604/99.02 |
| 6,350,252 B2 | 2/2002 | Ray et al. |
| 6,440,097 B1 | 8/2002 | Kupiecki |
| 6,454,775 B1 | 9/2002 | Demarais et al. |
| 6,458,096 B1 | 10/2002 | Briscoe et al. |
| 6,511,492 B1 | 1/2003 | Rosenbluth et al. |
| 6,514,273 B1 | 2/2003 | Voss et al. |
| 6,530,935 B2 | 3/2003 | Wensel et al. |
| 6,542,781 B1 | 4/2003 | Koblish et al. |
| 6,544,217 B1 | 4/2003 | Gulachenski |
| 6,547,754 B1 | 4/2003 | Evans et al. |
| 6,558,401 B1 | 5/2003 | Azizi |
| 6,575,933 B1 | 6/2003 | Wittenberger et al. |
| 6,589,206 B1 | 7/2003 | Sharkawy et al. |
| 6,610,077 B1 | 8/2003 | Hancock et al. |
| 6,620,179 B2 | 9/2003 | Boock et al. |
| 6,626,861 B1 | 9/2003 | Hart et al. |
| 6,638,245 B2 | 10/2003 | Miller et al. |
| 6,660,014 B2 | 12/2003 | Demarais et al. |
| 6,666,874 B2 | 12/2003 | Heitzmann et al. |
| 6,679,860 B2 | 1/2004 | Stiger |
| 6,685,722 B1 | 2/2004 | Rosenbluth et al. |
| 6,711,444 B2 | 3/2004 | Koblish |
| 6,743,208 B1 * | 6/2004 | Coyle ..................... 604/164.13 |
| 6,824,545 B2 | 11/2004 | Sepetka et al. |
| 6,945,977 B2 | 9/2005 | Demarais et al. |
| 7,004,954 B1 | 2/2006 | Voss et al. |
| 7,058,456 B2 | 6/2006 | Pierce |
| 7,070,576 B2 | 7/2006 | O'Brien et al. |
| 7,087,039 B1 | 8/2006 | Cox et al. |
| 7,179,269 B2 | 2/2007 | Welch et al. |
| 7,182,755 B2 | 2/2007 | Tal |
| 7,186,237 B2 | 3/2007 | Meyer et al. |
| 7,244,270 B2 | 7/2007 | Lesh |
| 7,250,042 B2 | 7/2007 | Kataishi et al. |
| 7,306,617 B2 | 12/2007 | Majercak |
| 7,338,501 B2 | 3/2008 | Teague et al. |
| 7,377,931 B2 | 5/2008 | Bagaoisan |
| 7,462,183 B2 | 12/2008 | Behl et al. |
| 7,507,246 B2 | 3/2009 | McGuckin et al. |
| 7,517,352 B2 | 4/2009 | Evans et al. |
| 7,758,604 B2 | 7/2010 | Wu et al. |
| 7,819,887 B2 | 10/2010 | McGuckin et al. |
| 7,862,576 B2 | 1/2011 | Gurm |
| 7,873,404 B1 | 1/2011 | Patton |
| 7,879,066 B2 | 2/2011 | Desai et al. |
| 7,883,516 B2 | 2/2011 | Huang et al. |
| 8,043,313 B2 | 10/2011 | Krolik et al. |
| 2001/0031981 A1 | 10/2001 | Evans et al. |
| 2002/0010487 A1 | 1/2002 | Evans et al. |
| 2002/0133117 A1 | 9/2002 | Zadno-Azizi et al. |
| 2002/0177870 A1 | 11/2002 | Sepetka et al. |
| 2003/0004542 A1 | 1/2003 | Wensel et al. |
| 2003/0009190 A1 | 1/2003 | Kletschka et al. |
| 2003/0163158 A1 | 8/2003 | White |
| 2004/0006361 A1 | 1/2004 | Boyle et al. |
| 2004/0133232 A1 | 7/2004 | Rosenbluth et al. |
| 2004/0181150 A1 | 9/2004 | Evans et al. |
| 2004/0236363 A1 | 11/2004 | Kieturakis et al. |
| 2004/0243156 A1 | 12/2004 | Wu et al. |
| 2004/0243167 A1 | 12/2004 | Tanaka et al. |
| 2005/0038383 A1 | 2/2005 | Kelley et al. |
| 2005/0059993 A1 | 3/2005 | Ramzipoor et al. |
| 2005/0131453 A1 | 6/2005 | Parodi |
| 2005/0288632 A1 | 12/2005 | Willard |
| 2006/0009784 A1 | 1/2006 | Behl et al. |
| 2006/0036277 A1 | 2/2006 | Kieturakis et al. |
| 2006/0074442 A1 | 4/2006 | Noriega et al. |
| 2006/0106407 A1 | 5/2006 | McGuckin et al. |
| 2006/0200047 A1 | 9/2006 | Galdonik et al. |
| 2006/0253145 A1 | 11/2006 | Lucas |
| 2007/0016244 A1 | 1/2007 | Behl et al. |
| 2007/0038225 A1 | 2/2007 | Osborne |
| 2007/0083158 A1 | 4/2007 | Hirszowicz et al. |
| 2007/0129752 A1 | 6/2007 | Webler et al. |
| 2007/0239182 A1 | 10/2007 | Glines et al. |
| 2007/0293935 A1 * | 12/2007 | Olsen et al. .................. 623/1.12 |
| 2008/0064930 A1 | 3/2008 | Turliue |
| 2008/0125798 A1 | 5/2008 | Osborne et al. |
| 2008/0177277 A1 | 7/2008 | Huang et al. |
| 2008/0200873 A1 | 8/2008 | Espinosa et al. |
| 2008/0228209 A1 | 9/2008 | DeMello et al. |
| 2008/0262487 A1 | 10/2008 | Wensel et al. |
| 2008/0269798 A1 | 10/2008 | Ramzipoor et al. |
| 2008/0306440 A1 | 12/2008 | Hirszowicz et al. |
| 2009/0018549 A1 | 1/2009 | Desai et al. |
| 2009/0018569 A1 | 1/2009 | Desai et al. |
| 2009/0076539 A1 | 3/2009 | Valaie |
| 2010/0036312 A1 | 2/2010 | Krolik et al. |
| 2010/0036410 A1 | 2/2010 | Krolik et al. |
| 2010/0137892 A1 | 6/2010 | Krolik et al. |
| 2011/0093000 A1 | 4/2011 | Ogle et al. |
| 2011/0125132 A1 | 5/2011 | Krolik et al. |
| 2012/0109057 A1 | 5/2012 | Krolik et al. |
| 2012/0197193 A1 | 8/2012 | Krolik et al. |

FOREIGN PATENT DOCUMENTS

| | | |
|---|---|---|
| JP | S62-233168 A | 10/1987 |
| JP | S63-192457 A | 8/1988 |
| JP | H03-080872 A | 4/1991 |
| JP | H08-509397 A | 10/1996 |
| JP | 2004-136103 A | 5/2004 |
| JP | 2008-504067 A | 2/2008 |
| WO | WO-94/18894 A1 | 9/1994 |
| WO | 2008117256 | 10/2008 |
| WO | 2008117257 | 10/2008 |

OTHER PUBLICATIONS

PCT International Search Report and Written Opinion for PCT/US2009/049639, Applicant: HotSpur Technologies, Inc., Forms PCT/ISA/220, PCT/ISA/210, and PCT/ISA/237: dated Feb. 1, 2010, 14 pages.

Extended European Search Report for European Application No. 09774584.8, dated Oct. 17, 2013.

Communication Pursuant to Article 94(3) EPC mailed Jun. 18, 2014, as received in European Patent Application No. 09774584.8.

Examination Report mailed Jun. 23, 2014, as received in Singaporean Patent Application No. 2010090801.

First Office Action mailed Jul. 16, 2013, as received in Chinese Patent Application No. 201080040808.2, and an English language summary thereof.

First Office Action mailed Jul. 23, 2013, as received in Japanese Patent Application No. 2011-512752, and an English language summary thereof.

First Office Action mailed Jun. 3, 2014, as received in Japanese Patent Application No. 2012-521865.

First Office Action mailed Nov. 1, 2012, as receiving in Chinese Patent Application No. 200980129911.1, and an English language translation thereof.

International Search Report and Written Opinion mailed Dec. 6, 2012, as received in International Application No. PCT/US2012/025734.

International Search Report and Written Opinion mailed Jan. 27, 2010, as received in International Application No. PCT/US2009/046659.

(56) References Cited

OTHER PUBLICATIONS

International Search Report and Written Opinion mailed Mar. 18, 2013, as received in International Application No. PCT/US2012/061672.
Invitation to Respond to Written Opinion mailed Nov. 8, 2012, as received in Singaporean Patent Application No. 201009080 1.
Notice of Rejection mailed Mar. 4, 2014, as received in Japanese Patent Application No. 2011-512752, and an English language summary thereof.
Notice of Rejection mailed Sep. 3, 2013, as received in Japanese Patent Application No. 2011-516896, and an English language summary thereof.
Office Action mailed Sep. 13, 2012, as received in Chinese Patent Application No. 200980134164.0.
Patent Examination Report No. 1 mailed Mar. 13, 2013, as received in Australian Patent Application No. 2009266808.
Second Office Action mailed Mar. 19, 2013, as received in Chinese Patent Application No. 201080040808.2, and an English language summary thereof.

* cited by examiner

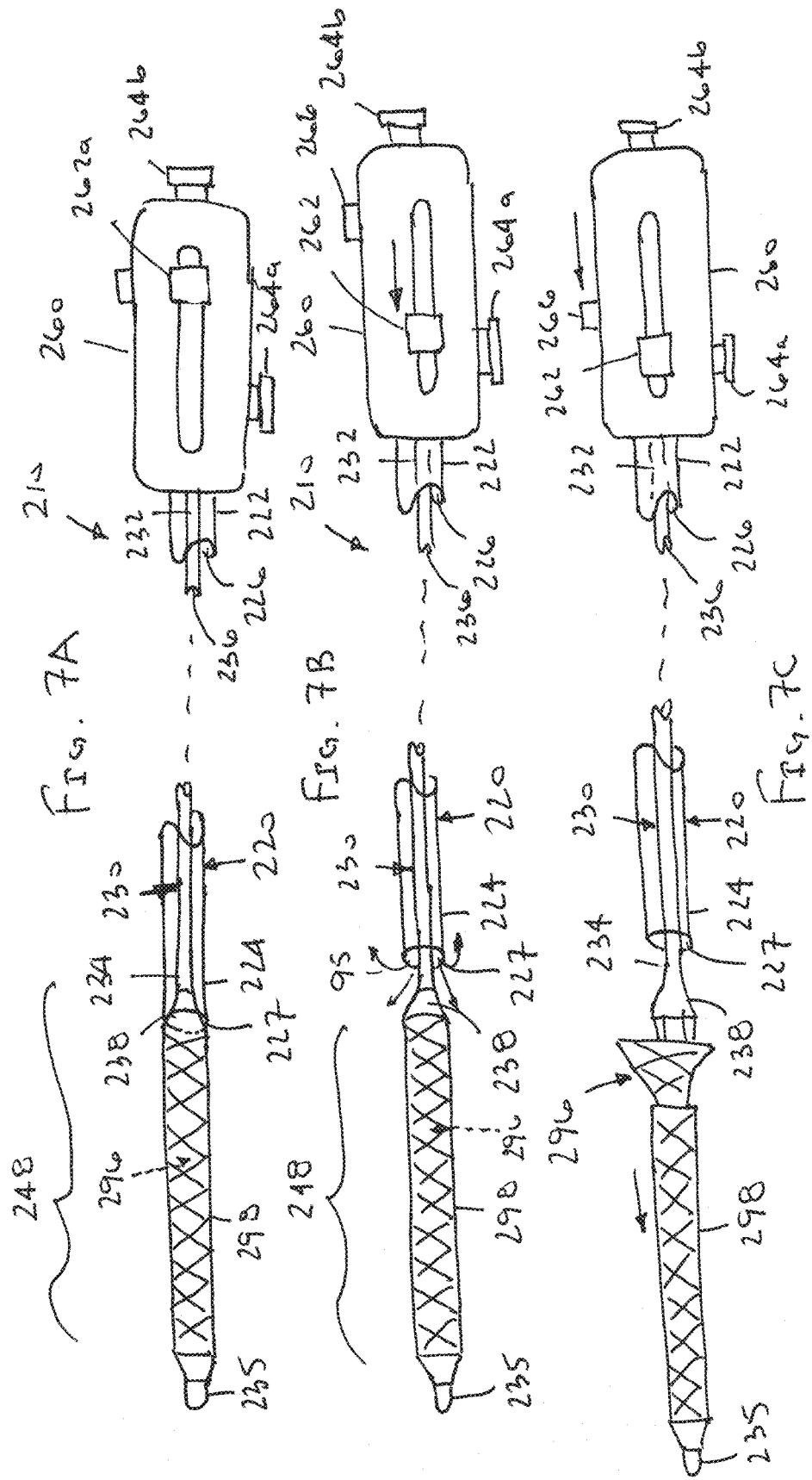

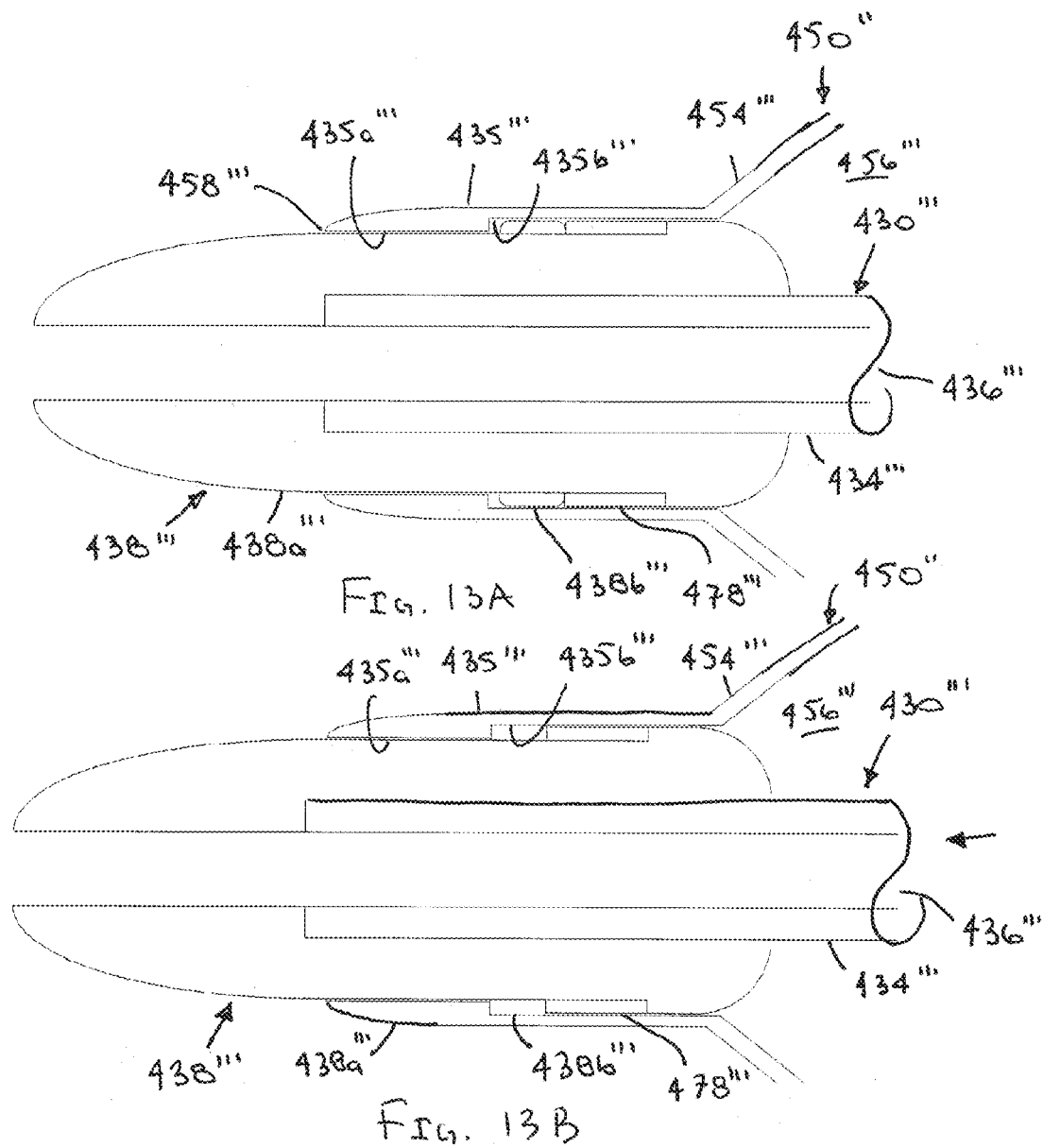

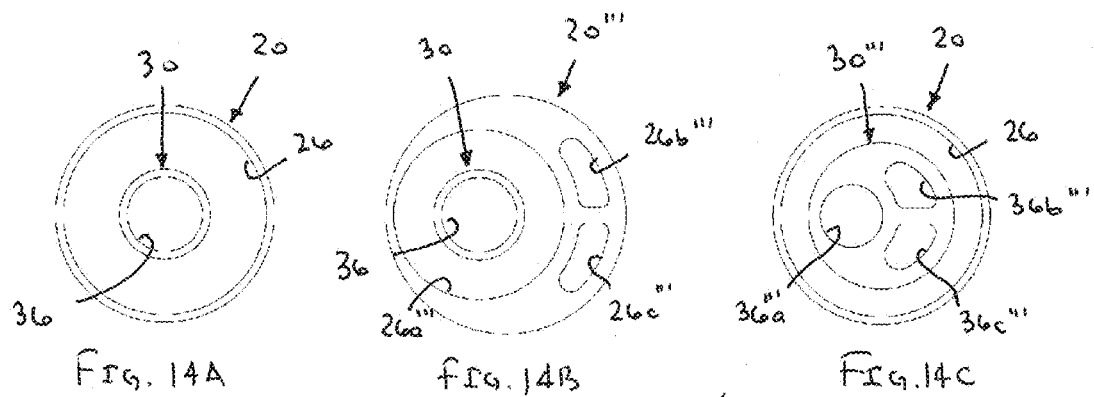
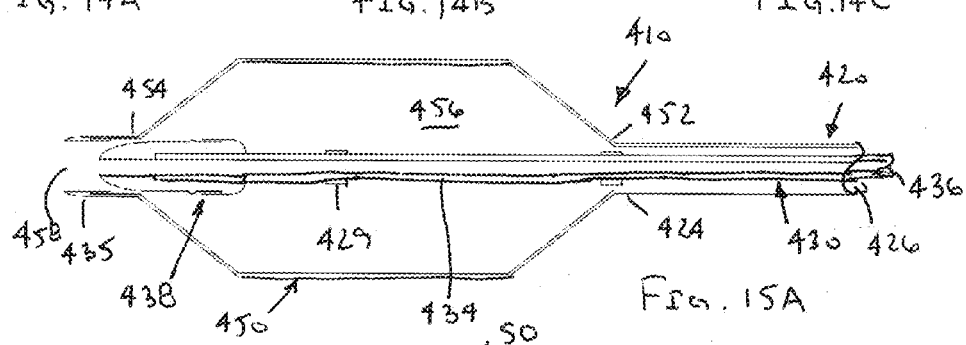
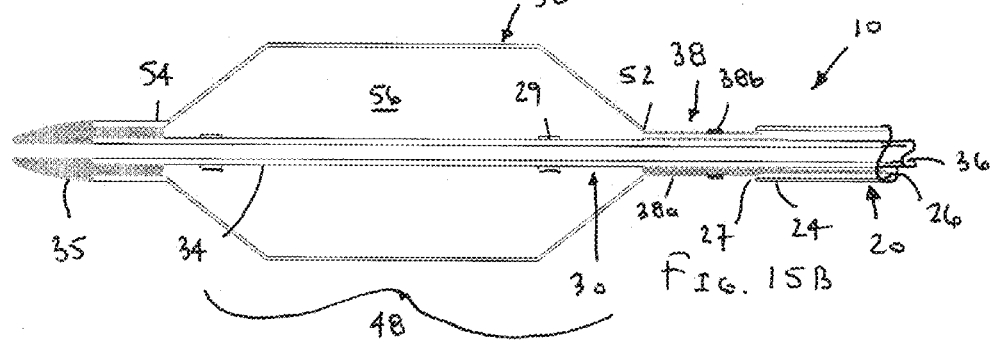

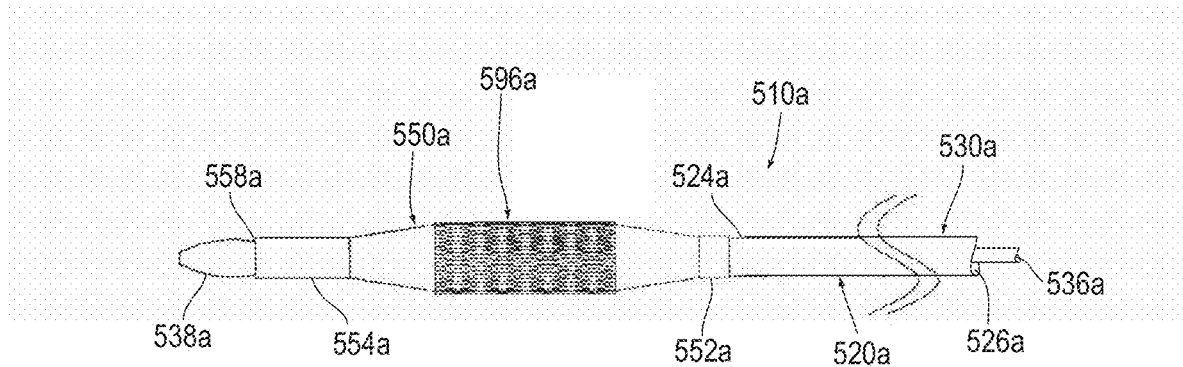
FIG. 18A
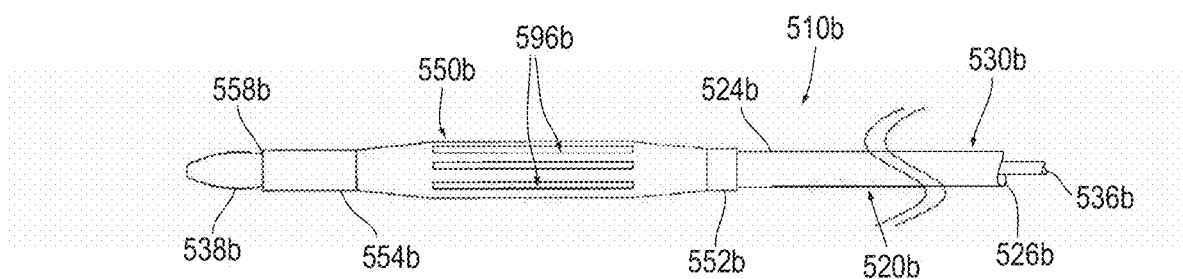
FIG. 18B
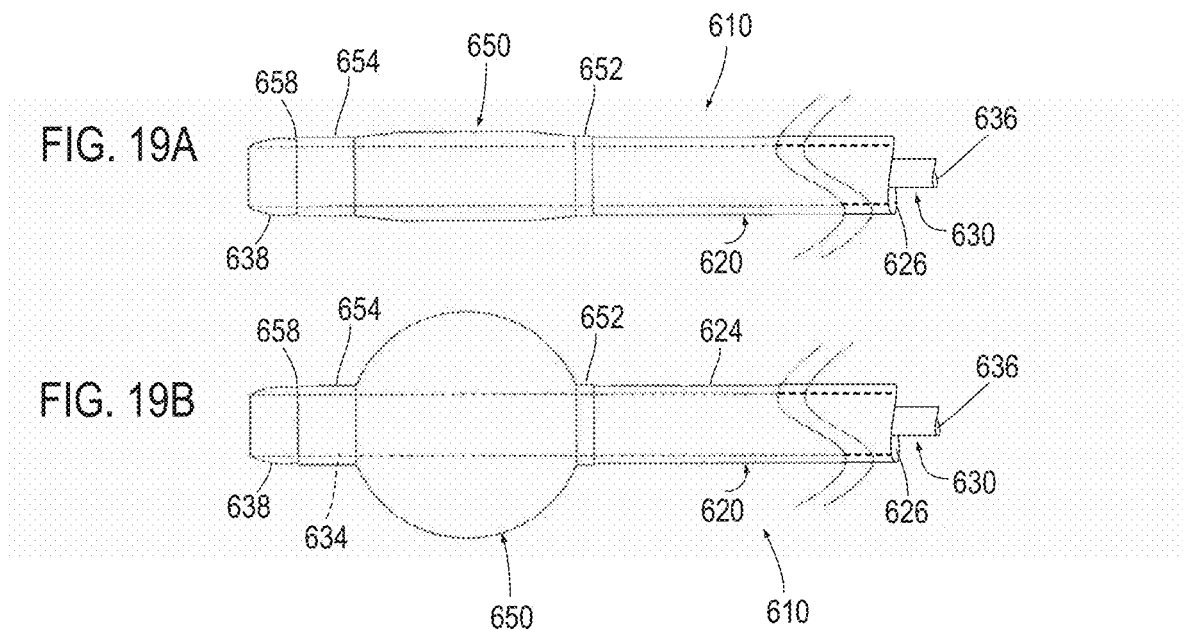
FIG. 19A
FIG. 19B

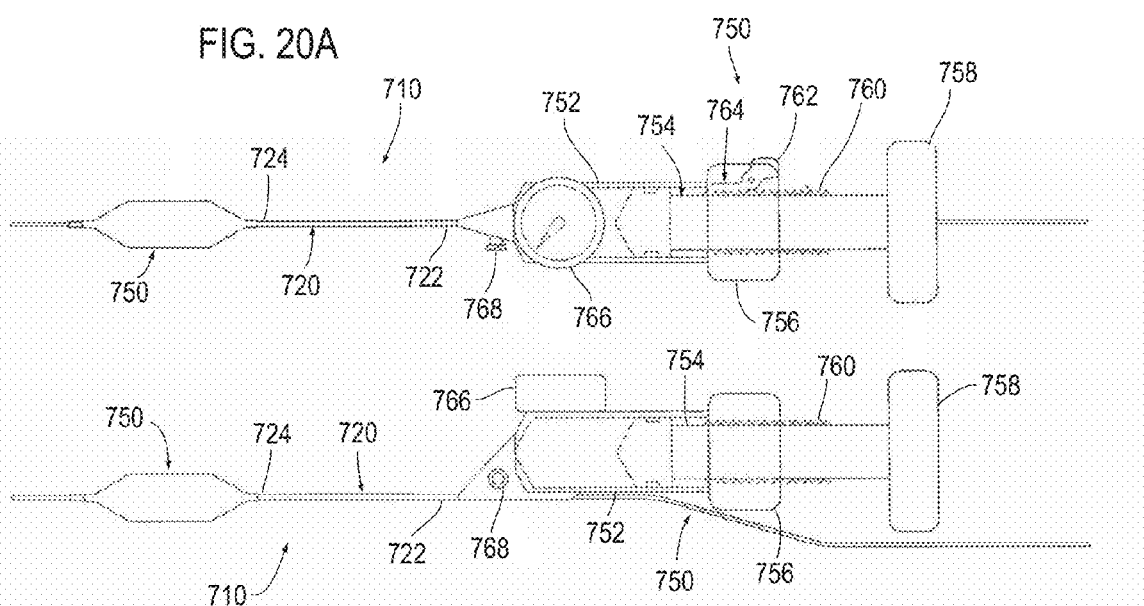

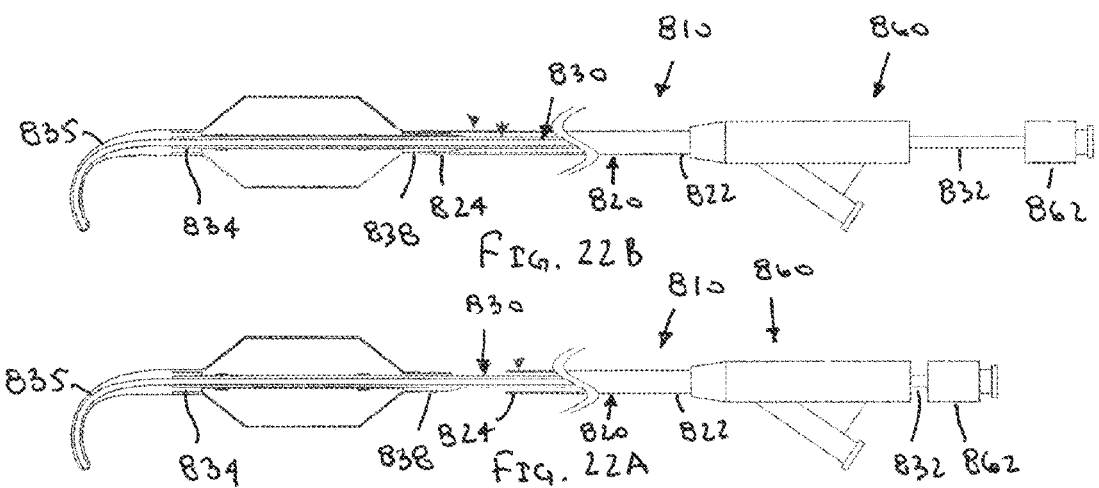

APPARATUS AND METHODS FOR TREATING OBSTRUCTIONS WITHIN BODY LUMENS

RELATED APPLICATIONS

This application claims benefit of co-pending provisional application Ser. Nos. 61/402,166, filed Aug. 25, 2010, 61/463,537, filed Feb. 9, 2011, and 61/520,927, filed Jun. 17, 2011, and is a continuation-in-part of application Ser. No. 12/843,004, filed Jul. 23, 2010, which claims benefit of provisional application Ser. Nos. 61/271,627, filed Jul. 23, 2009, 61/283,035, filed Nov. 25, 2009, 61/342,755, filed Apr. 19, 2010, and 61/397,854, filed Jun. 17, 2010, and is a continuation-in-part of co-pending application Ser. No. 12/497,135, filed Jul. 2, 2009, which claims benefit of U.S. provisional application Ser. Nos. 61/153,620, filed Feb. 18, 2009, 61/214, 667, filed Apr. 27, 2009, and 61/215,732, filed May 8, 2009. The entire disclosures of these applications are expressly incorporated by reference herein.

FIELD OF THE INVENTION

The present invention relates generally to apparatus for performing procedures within a body lumen of a patient, e.g., for removing or treating obstructive material within a tubular graft, aorto-venous fistula, blood vessel, and the like. More particularly, the present invention relates to apparatus, e.g., catheters, for infusing fluids into a body lumen during a medical procedure, for example, procedures involving removing or otherwise capturing thrombus or other obstructive material within a body lumen, dilating a body lumen, and/or delivering a prosthesis, and to methods for making and using such apparatus.

BACKGROUND

Flow within a blood vessel or other body lumen within a patient's vasculature may become constricted or ultimately interrupted for a variety of reasons. For example, a vessel may gradually narrow due to inflammation and/or cell proliferation. In addition, thrombus may form due to such narrowing or other flow problems within a vessel.

For example, an aorto-venous graft may be implanted in an arm of a patient experiencing kidney failure, e.g., to facilitate dialysis treatment. Such grafts may be a fistula formed directly in the patient's body, e.g., through tissue between an adjacent artery and vein or other vessels, may be a xenograft implanted between two vessels, or may be a synthetic graft. Such grafts only have a limited life cycle due to inflammation, thrombus formation, and the like. Once such a graft becomes sufficiently occluded or otherwise deteriorates, a new graft must be implanted at a new location for subsequent treatment.

Accordingly, apparatus and methods for removing material from aorto-venous grafts, blood vessels, or other body lumens and/or otherwise treating body lumens would be useful.

SUMMARY

The present invention is directed to apparatus for performing a procedure within a body lumen of a patient, e.g., a tubular graft, aorto-venous fistula, blood vessel, and the like. More particularly, the present invention is directed to apparatus and methods for infusing fluids into a body lumen during a medical procedure, and/or for removing or otherwise capturing thrombus or other obstructive material within a body lumen, e.g., procedures involving removing obstructive or other material, dilating a body lumen, delivering a prosthesis within a body lumen, and/or other procedures.

In accordance with a first embodiment, an apparatus is provided for performing a procedure within a body lumen that is operable in different modes to perform various functions, e.g., possibly reducing the number of device exchanges during a procedure. For example, the apparatus may include a shaft including a proximal end, a distal end sized for introduction into a body lumen, a lumen extending therebetween, and a balloon on the distal end having an interior communicating with the lumen. The apparatus may also include a valve on the distal end of the shaft that selectively opens or closes an outlet communicating with the lumen. With the valve open, fluid introduced into the lumen may exit the outlet into a body lumen adjacent the distal end. With the valve closed, fluid introduced into the lumen may expand the balloon from a contracted condition to an expanded condition, e.g., to dilate an obstruction within a body lumen, to remove thrombus or other material within the body lumen, to deliver a prosthesis carried on the distal end, to deliver drugs or other agents carried on the distal end, and the like.

In accordance with another embodiment, an apparatus is provided for treating a body lumen that includes an elongate tubular outer member including a proximal end, a distal end, and a first lumen extending between the proximal and distal ends; an expandable balloon including a proximal end secured to the tubular member distal end, and a distal end including an outlet, the balloon including an interior communicating with the first lumen and the balloon outlet. An elongate inner member is slidably disposed within the first lumen that includes a proximal end adjacent the tubular member proximal end, and a distal end extending into, through, and/or beyond the balloon. The balloon and inner member may include cooperating features providing a valve for selectively opening and closing the balloon outlet. For example, the valve may include a sealing member on the distal end of the inner member sized to be engaged with the balloon distal end to substantially seal the outlet from fluid flow.

The inner member may be movable between a first position wherein the sealing member is spaced apart from the balloon distal end such that fluid introduced through the first lumen passes through the balloon interior and out the balloon outlet, and a second position wherein the sealing member substantially seals the balloon outlet such that fluid introduced through the first lumen enters the balloon interior to expand the balloon.

Optionally, the inner member may be biased towards one of the first and second positions, but may be selectively directed to the other of the first and second positions. For example, a tensioning element may be provided within the balloon interior, e.g., coupled between the balloon and the inner member. In one embodiment, where the sealing member is disposed within the balloon interior, the tensioning element may bias the balloon distal end distally away from the sealing member, e.g., to prevent the balloon distal end from moving proximally when the sealing member is actuated to open the valve. For example, the tensioning element may be a compression spring that is compressed when the inner member is directed distally to close the valve, and may be allowed to partially relax when the inner member is directed proximally to open the valve.

In another embodiment, where the sealing member is disposed distally beyond the balloon outlet, the tensioning element may bias the balloon distal end distally, e.g., to engage the sealing member with the balloon distal end to substantially seal the outlet. For example, the tensioning element may be coupled between a spring stop on the balloon and a collar or other attachment member on the inner member. When the inner member is advanced distally to open the outlet, the tensioning element may be compressed between the spring stop and the collar. When the inner member is released or directed to close the outlet, the tensioning element may ensure that the balloon distal end does not migrate proximally and/or may automatically direct the inner member proximally to reseal or enhance resealing the outlet with the sealing member.

If desired, the distal end of the balloon may include a distal tip shaped and/or configured to facilitate sealing and/or opening the outlet. For example, in one embodiment, the sealing member may include a tapered proximal end, and the distal tip may be flared outwardly away from the balloon such that the tapered proximal end of the sealing member may be seated at least partially in the flared distal tip. Such an embodiment may increase surface contact between the sealing member and the distal end, which may enhance sealing the outlet. In addition or alternatively, the flared distal tip may maximize the free area of the outlet when the sealing member is directed away from the outlet.

In another embodiment, a distal tip may be provided that is resiliently expandable, e.g., to increase surface contact between the sealing member and the distal end of the balloon to enhance sealing the outlet. For example, the distal tip may be relatively thin compared to the distal end of the balloon such that, when the sealing member is directed proximally into the distal tip, the distal tip may expand and conform to the shape of the sealing member. When the sealing member is directed distally to open the outlet, the distal tip may resiliently return to its original size and/or shape.

Optionally, any of the apparatus herein may include a helical member extending helically around the inner member within the balloon interior and including a first end coupled to the tubular member distal end and a second end coupled to the inner member distal end. In this embodiment, the inner member may be movable to a third position in which the inner member distal end is directed towards the tubular member distal end to cause the helical member to compress axially and expand radially outwardly, thereby expanding the balloon to an expanded helical shape.

Optionally, in any of these embodiments, a coating may be provided on an inner surface of at least a portion of the balloon distal end, distal tip, and/or the sealing member, e.g., to reduce friction between the balloon distal end and/or distal tip and the sealing member in the second position.

In another option, in any of these embodiments, the distal end of the balloon may be sized to provide a predetermined resistance to fluid flow therethrough. For example, a spring stop or other feature within the distal end may partially obstruct the passage through the distal end leading to the outlet. Thus, if desired, with the outlet open, the distal end may provide sufficient resistance to fluid flow therethrough that fluid delivered into the balloon interior may at least partially expand the balloon as well as deliver fluid through the outlet into a body lumen.

In yet another option, in any of these embodiments, the inner member may include a "J" or other curved tip that extends beyond the balloon, e.g., to facilitate guiding the tip, and consequently, the distal end of the apparatus into a branch from a body lumen. In this variation, the inner member may be partially decoupled from the tubular member such that the inner member may be rotated to change the orientation of the curved tip. For example, the inner member may be rotatable less than three hundred sixty degrees to limit rotation, e.g., to prevent excess torque from being applied to the inner member.

In still another option, the inner member may include a distal tip that extends beyond the balloon, and that includes a guidewire lumen therein. For example, the distal tip may include a distal opening and a proximal sidewall opening and the guidewire lumen may extend therebetween, e.g., to provide a "rapid-exchange" guidewire lumen on the distal tip. Alternatively, the inner member may include a guidewire lumen that extends between the proximal and distal ends of the inner member.

In accordance with still another embodiment, an apparatus is provided for treating a body lumen that includes an outer member including a proximal end, a distal end sized for introduction into a body lumen, and a first lumen extending between the proximal end and an outlet in the distal end. An inner member is slidably disposed within the first lumen that includes a proximal end adjacent the outer member proximal end, a distal portion extending distally beyond the outer member distal end, and a sealing member on or adjacent the distal portion. The inner member may be movable between a first position wherein the sealing member is spaced from the outlet of the outer member such that fluid introduced through the first lumen passes through the outlet into a region around the apparatus, and a second position wherein the sealing member substantially seals the outlet.

In one embodiment, an expandable balloon is provided on the distal portion and the sealing member includes one or more passages therethrough such that, when the inner member is in the second position to seal the outlet, fluid introduced through the first lumen passes through the one or more passages and enters the balloon interior to expand the balloon. Alternatively, the distal portion may include one or more passages communicating between the sealing member and a distal end of the inner member such that, when the inner member is in the second position to seal the outlet, fluid introduced through the first lumen passes through the one or more passages and into the body lumen distally beyond the distal portion. In addition or alternatively, other treatment elements may be provided on the distal portion instead of or in addition to the balloon, such as a stent, stent-graft, prosthetic valve, and the like.

In accordance with yet another embodiment, a method is provided for performing a procedure that includes introducing a distal end of an apparatus into a body lumen of a patient, the apparatus including an outer tubular member including a first lumen extending between a proximal end and an outlet at a distal end thereof, an elongate inner member slidable within the first lumen and including a distal portion extending beyond the tubular member outlet, and a valve member disposed on or adjacent the inner member. The distal ends of the outer and inner members may be introduced into a body lumen, e.g., via the patient's vasculature or other passages. An actuator on a proximal end of the apparatus may be activated to move the inner member to a first position wherein the valve member is located away from the tubular member outlet, and fluid may be delivered through the first lumen such that the fluid exits the outlet proximal to the distal portion into the body lumen.

Thereafter, the inner member may be directed towards a second position wherein the valve member substantially seals the outlet. A treatment element on the distal portion may then be manipulated to perform a medical procedure within the body lumen. For example, in one embodiment, a balloon may be provided on the distal portion, and, in the second position, fluid delivered through the first lumen enters the balloon interior to expand the balloon. Optionally, a spring element may be provided within the balloon interior that provides sufficient bias to ensure that the valve member substantially engages the tubular member outlet in the second position. Alternatively, the spring element may have sufficient bias such that, when the actuator is released after directing the inner member to the first position, the spring element automatically directs the inner member towards the second position to substantially seal the outlet with the valve member.

If desired, the valve may be opened and fluid may be delivered through the outlet into the body lumen one or more times, e.g., while manipulating the apparatus, for example, to position the distal portion at a desired location, to observe the patient's anatomy, e.g., using external imaging, and the like.

Once the distal portion is positioned at a desired location, one or more procedures may be performed within the body lumen. For example, the distal portion may include one or more treatment elements for treating the body lumen. In one embodiment, the distal portion may carry a balloon in a contracted condition that has an interior communicating with one or more passages in the sealing member. For example, with the sealing member in the second position sealing the outlet, fluid delivered through the first lumen may pass through the passage(s) into the interior of the balloon, thereby expanding the balloon from the contracted condition to an enlarged condition, e.g., for dilating a lesion or otherwise treating a body lumen.

Optionally, the balloon may carry one or more therapeutic and/or diagnostic agents, e.g., embedded within or otherwise carried on an outer surface of the balloon, which may pressed against the wall of the body lumen. If desired, the balloon may include one or more features to enhance penetration into the wall of the body lumen, e.g., to enhance delivery of the agent(s) into the wall.

In another option, the balloon may be directed to an expanded helical shape within the body lumen, e.g., before or after expanding the balloon to the enlarged condition, and the balloon may be directed along a wall of the body lumen in the expanded helical shape to remove material from the wall of the body lumen.

In another embodiment, a prosthesis may be carried by the distal portion, e.g., over the balloon. For example, a stent, stent-graft, prosthetic valve, or other prosthesis, may be carried by the distal portion in a compressed state, and the balloon may be inflated to expand the prosthesis within the body lumen, e.g., to dilate the body lumen and/or deploy the prosthesis within the body lumen.

In yet another embodiment, a self-expanding prosthesis may be carried on the distal portion. In this embodiment, the distal portion may not include a balloon, but may include a removable constraint that may overly the prosthesis or otherwise maintain the prosthesis in a compressed state for delivery into the body lumen. Once the prosthesis is positioned at a desired location, e.g., after opening the valve and delivering contrast or other fluid into the body lumen, the constraint may be removed to allow the prosthesis to expand within the body lumen. Optionally, if a balloon is provided on the distal portion, the balloon may be expanded, e.g., by delivering fluid through passage(s) in the sealing member from the first lumen with the inner member in the second position, to further expand the prosthesis, if desired.

In still another embodiment, the distal portion may include one or more passages communicating between the sealing member and one or more outlets at a distal tip of the inner member. For example, with the valve open in the first position, fluid delivered through the first lumen may exit the outlet into the body lumen proximal to the distal portion. With the valve closed in the second position, fluid delivered through the first lumen may pass through the passage(s) in the distal portion and exit the outlet(s) into the body lumen distally beyond the distal portion. Thus, in this embodiment, contrast or other fluid may be selectively delivered on either side of the distal portion and/or a treatment element carried thereon during a procedure.

In accordance with yet another embodiment, a method is provided for treating a body lumen of a patient using a balloon apparatus including an outer member that includes a first lumen extending between a proximal end and an outlet on a distal end thereof, an inner member slidable within the first lumen, and a balloon attached to a distal end of the inner member beyond the outer member distal end. The distal end of the outer member may be introduced into a body lumen with the balloon in a contracted condition. The inner member may be directed between a first position wherein a sealing member on the inner member is spaced apart from the outlet, and a second position wherein the sealing member substantially seals an outlet in the outer member distal end communicating with the first lumen.

The inner member may be directed to the first or distal position, e.g., using an actuator on a proximal end of the outer member, consequently directing the sealing member away from and opening the outlet. Fluid may be delivered through the first lumen such that the fluid passes through the outlet into the body lumen. Optionally, the inner member may be directed to an intermediate position wherein some of the fluid is delivered into the body lumen and some of the fluid passes through one or more passages in the sealing member into the balloon interior to at least partially expand the balloon.

If desired, the inner member may be directed towards the second or proximal position to substantially seal the outlet with the sealing member, and fluid may be delivered through the first lumen with the outlet substantially sealed, thereby delivering the fluid through the one or more passages in the sealing member to expand the balloon from the contracted condition to an enlarged condition. In exemplary embodiments, the balloon may be used to dilate or otherwise treat a body lumen, to deliver a prosthesis and/or one or more agents, and the like. After sufficient treatment, the fluid may be aspirated from the interior of the balloon through the one or more passages and first lumen to return the balloon to the contracted condition.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 7A and 7B are side views of still another exemplary embodiment of an apparatus operable in a first mode for infusing fluid into a body lumen (FIG. 7A) and a second mode for delivering a prosthesis and/or performing a procedure within the body lumen (FIG. 7B).

FIG. 7C is a side view of the apparatus of FIGS. 7A and 7B, showing a constraint being advanced to deploy a prosthesis carried by the apparatus.

FIGS. 13A and 13B are details of a distal end of yet another alternative embodiment of the apparatus of FIG. 9, showing a valve seal enhancing sealing of an outlet of the balloon.

FIGS. 14A-14C are cross-sectional views of alternative configurations of inner and outer members that may be provided on any of the apparatus herein.

FIGS. 15A and 15B are side views of distal ends of alternative embodiments of apparatus including a balloon and a valve member positionable at an intermediate condition in which fluid may be infused into a body lumen simultaneously with delivering fluid into the interior of the balloon.

FIGS. 18A-18C are side views of distal ends of alternative embodiments of the apparatus of FIG. 17.

FIGS. 19A and 19B are side views of a distal end of an exemplary embodiment of an introducer sheath including a balloon and sealing member.

FIGS. 20A and 20B are side and top views, respectively, of another exemplary embodiment of an apparatus including an integrated inflation device.

FIGS. 22A and 22B are side views of the apparatus of FIGS. 21A-21C, showing a valve thereof in closed and open positions, respectively.

DETAILED DESCRIPTION OF THE EXEMPLARY EMBODIMENTS

Figure 1:
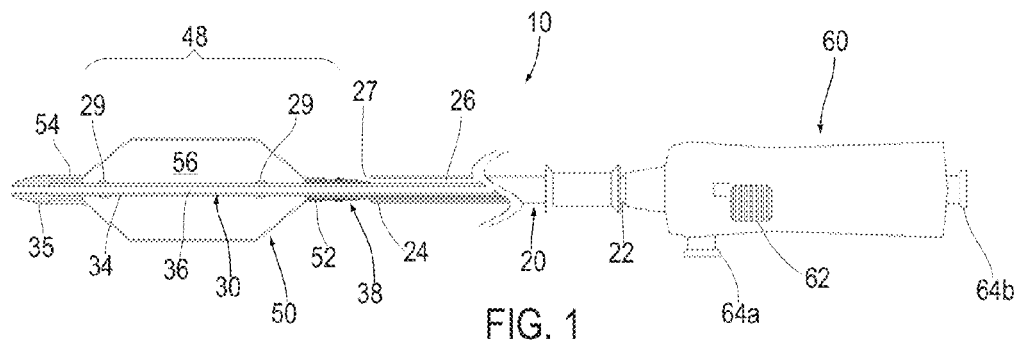
FIG. 1 is a side view of a first exemplary embodiment of an apparatus including a balloon for treating a body lumen, the apparatus operable in a first mode for infusing fluid into the body lumen and a second mode for inflating the balloon and/or otherwise performing a procedure within the body lumen.
Figure 2A:
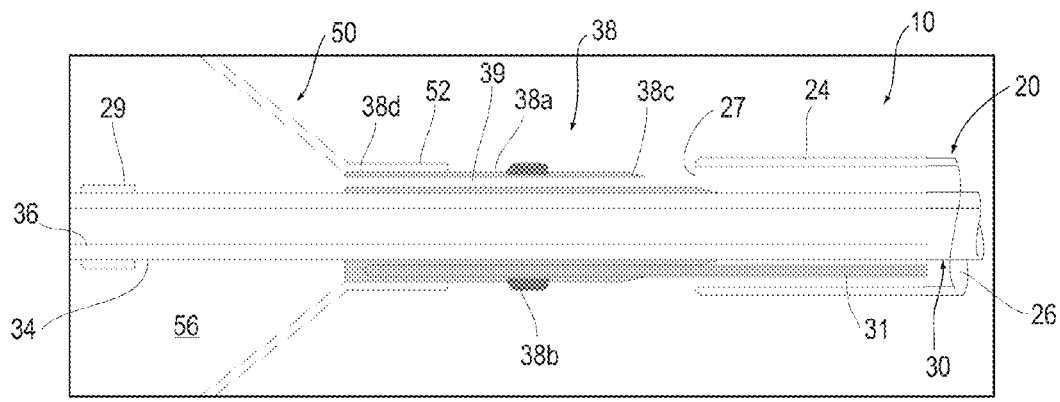
FIG. 2A is a side view of the apparatus of FIG. 1 in the first mode for infusing fluid into a body lumen.
Figure 2B:
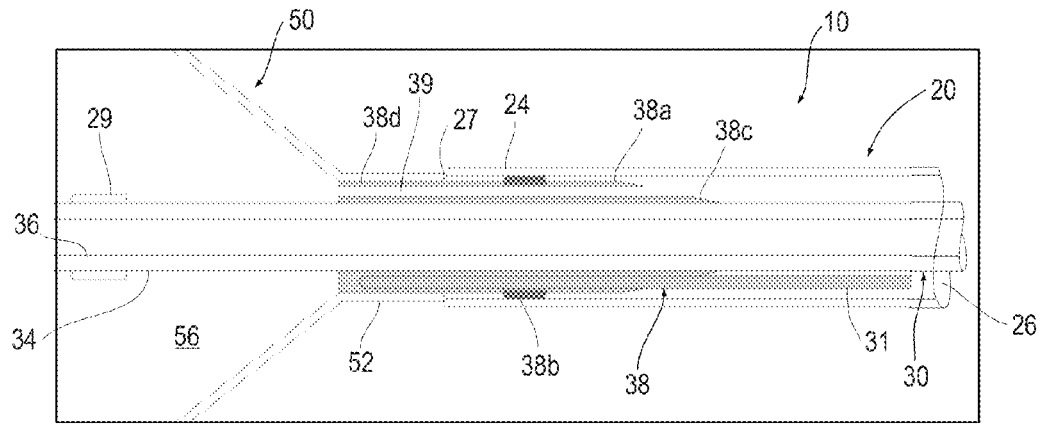
FIG. 2B is a side view of the apparatus of FIG. 1 in the second mode for inflating the balloon within a body lumen.

Turning to the drawings, FIGS. 1-2B show a first exemplary embodiment of an apparatus 10 for treating a body lumen, e.g., for infusing fluid into a body lumen, such as a blood vessel, aorto-venous fistula, tubular graft, and the like (not shown), and/or for performing a procedure within the body lumen, e.g., dilating a stenosis or other obstruction within the body lumen, removing thrombus, objects, and/or obstructive material from within the body lumen, delivering a stent, stent-graft, prosthetic valve, or other prosthesis (also not shown), delivering one or more agents into the body lumen, and the like. Generally, the apparatus 10 includes a catheter, sheath, or other tubular outer member 20, a shaft or other elongate inner member 30, and an expandable balloon or other treatment element 50 carried by the inner and/or outer members 20, 30, e.g., on a distal portion 48 of the inner member 30 shown in FIG. 1.

The apparatus 10 may be operable in multiple modes, for example, to perform various treatments or other functions within a body lumen, e.g., to reduce or eliminate the need to exchange multiple devices during a procedure within a body lumen. For example, the apparatus 10 may include a valve, e.g., including a sealing or valve member 38, operable in a first mode for infusing fluid into a body lumen (FIG. 2A), and a second mode to facilitate introduction into a patient's body and/or to inflate the balloon 50 (FIG. 2B), as described further below.

As best seen in FIG. 1, the outer member 20 includes a proximal end 22 coupled to a handle 60, a distal end 24 sized for introduction into a body lumen, and a first lumen 26 extending between the proximal end 22 and an outlet 27 in the distal end 24. The outer member 20 may have a substantially uniform construction along its length, or alternatively, the construction may be varied. For example, a proximal portion of the outer member 20 may be substantially rigid or semi-rigid to facilitate advancement of the apparatus 10 from the proximal end 22, and/or a distal portion of the outer member 20 may be flexible, e.g., to facilitate bending and/or advancement through tortuous anatomy without substantial risk of kinking or buckling. In exemplary embodiments, the outer member 20 may be formed from one or more materials such as metal, plastic, e.g., PEEK, Grilamed L25, and the like, or composite materials. The outer member 20 may have a length between about thirty and one hundred thirty centimeters (30-130 cm) and an outer diameter between about 1.2 and 2.0 millimeters, and the first lumen 26 may have a diameter between about 1.0 and 1.8 millimeters.

The inner member 30 also includes a proximal end (not shown), a distal end 34, and, optionally, may include a second lumen 36 extending between the proximal end and a distal tip 35, which may be sized to slidably receive a guide wire, or other rail (not shown) therethrough, e.g., having a diameter between about 0.3 and 1.0 millimeter. Alternatively, as shown in FIG. 3A, a distal tip 35" may be provided on the apparatus 10" (or any of the other embodiments herein) that includes a relatively short guidewire lumen 36" beyond the balloon 50." As shown, the guidewire lumen 36" may communicate between a distal port 36a" in the distal tip 35" and a proximal side port 36b" adjacent to the distal end 54" of the balloon 50." In this alternative, a guidewire (not shown) may be backloaded into the distal port 36a" through the guidewire lumen 36" and out the proximal port 36b", e.g., to provide a "rapid-exchange" lumen such that the guidewire need not be loaded through the entire length of the inner member 30." Thus, in this alternative, the second lumen 36 (shown in FIGS. 1-2B) may be omitted.

The inner member 30 may have a substantially uniform construction along its length, or alternatively, the construction may be varied, similar to the outer member 20. For example, the inner member 30 may be formed from a composite construction including a braided, helical, or other support structure, e.g., formed from metal, such as stainless steel, polymeric strong fiber, and the like, embedded in a polymeric matrix, e.g., a thermoset polymeric matrix, such as polyimide, that may resist the inner member 30 taking a shape set when bent or curved. Optionally, the inner member 30 may include a tether wire 31 coupled between the proximal and distal ends 32, 34, e.g., bonded or otherwise attached to the valve member 38 and/or balloon 50, as shown in FIGS. 2A and 2B. The tether wire 31 may be embedded in the shaft of the inner member 30 or may be free and/or external to the shaft other than at the valve member 38 and/or balloon 50, as shown. The tether wire 31 may be a high strength, relatively small cross-section wire or filament that may provide a safety feature to prevent the balloon 50 from becoming loose from the apparatus 10, e.g., if the inner member 30 were somehow broken between the proximal and distal ends 32, 34 during use.

Returning to FIG. 1, the inner member 30 is sized to be slidably received within the first lumen 26 of the outer member 20, e.g., such that an annular space is defined between the outer and inner members 20, 30 for passing one or more fluids therethrough, as described further below. The inner member 30 may have a length relative to the outer member 20 such that the inner member proximal end is received within or extends proximally beyond the outer member proximal end 22, e.g., into the handle 60, and the inner member distal end 34 extends distally beyond the outlet 27 of the outer member 20, e.g., to define the distal portion 48, as described further below. The distal tip 35 may have a rounded, tapered, and/or other shape, e.g., to provide a substantially atraumatic tip for the apparatus 10, similar to embodiments in the applications incorporated by reference herein.

The handle 60 may be coupled to or otherwise provided on the proximal end 22 of the outer member 20, e.g., attached by one or more of an interference fit, bonding with adhesive, sonic welding, cooperating connectors (not shown), and the like. An actuator 60 may be coupled to the proximal end of the inner member 30 for directing the inner member 30 axially relative to the outer member 20, e.g., to open or close the outlet 27 and/or to direct the apparatus 10 between the different modes, as described further elsewhere herein. The handle 60 may also include one or more ports 64, e.g., a first port 64a communicating with the first lumen 26, and a second port 64b communicating with the second lumen 36, similar to embodiments in the applications incorporated by reference herein.

The balloon 50 includes proximal and distal ends 52, 54 coupled to the distal portion 48 of the inner member 30, e.g., a distal end 54 attached to the inner member 30, e.g., adjacent the distal tip 35, a proximal end 52 attached to the distal end 34 of the inner member 30 proximal to the distal tip 35, thereby defining a substantially fluid-tight interior 56. For example, the distal end 54 of the balloon 50 may be attached or otherwise secured directly to the distal end 24 of the outer member 20 and/or to the distal tip 35 to provide a fluid-tight connection, e.g., by one or more of bonding with adhesive, interference fit, sonic welding, fusing, engagement with a surrounding sleeve or other connector (not shown), and the like.

The balloon 50 may be formed from elastic material, e.g., to provide a compliant or semi-compliant balloon that may be expanded to a variety of sizes and/or shapes, e.g., based on the amount of fluid and/or pressure within the interior 56. Alternatively, the balloon 50 may be formed from substantially inelastic material, e.g., to provide a non-compliant balloon that expands to a predetermined size when inflated substantially independent of pressure (once a minimum volume and/or pressure is introduced to achieve the predetermined size). Such a non-compliant balloon 50 may expand to the predetermined size even if inflated to relatively high pressures, e.g., until the balloon 50 bursts or otherwise ruptures, e.g., at pressures of at least ten atmospheres, twenty atmospheres, thirty atmospheres, and the like.

As best seen in FIGS. 2A and 2B, the sealing or valve member 38 is provided on or adjacent the distal portion 48 of the inner member 32, e.g., adjacent the proximal end 52 of the balloon 50. For example, the sealing member 38 may be attached to an outer surface of the inner member 30 and the proximal end 52 of the balloon 50 may be attached to the sealing member 38. As shown, the proximal end 52 of the balloon 50 extends at least partially over the sealing member 38 and may be attached to the sealing member 38, e.g., by bonding with adhesive, sonic welding, fusing, interference fit, an exterior collar (not shown), and the like. Thus, the proximal end 52 of the balloon 50 may have a substantially fluid-tight seal with the sealing member 38 and consequently the inner member 30.

The sealing member 38 generally has a size to at least partially enter the first lumen 26 of the outer member 20, e.g., such that the sealing member 38 may substantially seal the outlet 27 when the sealing member 38 is engaged with or received in the outlet 27 and/or first lumen 26. For example, as best seen in FIG. 2B, the sealing member 38 may include a valve body 38a and one or more annular valve seals 38b extending around the valve body 38a. Although only a single valve seal 38b is shown, it will be appreciated that a plurality of valve seals (not shown) may be provided that are spaced apart axially from one another along a length of the valve body 38a, e.g., to enhance the resulting seal.

The valve body 38a may have an outer diameter slightly smaller than the inner diameter of the first lumen 26 and/or outlet 27, e.g., such that the valve body 38a may freely enter the first lumen 26 through the outlet 27. The valve seal(s) 38b may have an outer diameter that is slightly larger than the inner diameter of the first lumen 26 such that the valve seal(s) 38b slidably engage the inner surface of the outer member 20 when the valve body 38a enters the first lumen 26. For example, the valve seal(s) 38b may be formed from resiliently flexible material, such as silicone or other elastomer, a low Durometer (e.g., 40 D) PEBAX material, polyurethane, and the like, that may be sufficiently compressible to accommodate sliding into the first lumen 26 without creating substantial friction, yet may resist deformation under substantial fluid pressure, e.g., to maintain a substantially fluid-tight seal against the inner wall of the outer member 20.

Alternatively, the valve seal(s) 38b may be formed from relatively harder, lubricious material that has mechanical compressibility, e.g., polyethylene tubular or other hollow structure that may bend in response to applied loads. The valve body 38a may be formed from a different material than the valve seal(s) 38b, e.g., to provide a more rigid base or support for the valve seal(s) 38a, or may be formed from the same material, e.g., integrally molded, or otherwise formed from a single piece of material. Thus, the valve seal(s) 38b may slidably engage the inner surface of the outer member 20 to provide a substantially fluid-tight seal without requiring excessive force that may otherwise jam or damage the apparatus 10 during use.

Optionally, the sealing member 38 may have a tapered shape to facilitate aligning and/or receiving the sealing member 38 within the outlet 27. For example, as shown in FIGS. 2A and 2B, the valve body 38a may include a tapered proximal end 38c to guide the sealing member 38 into the outlet 27 and first lumen 26, e.g., in case the outer and inner members 20, 30 become out of concentric alignment with one another during use.

Figure 3:
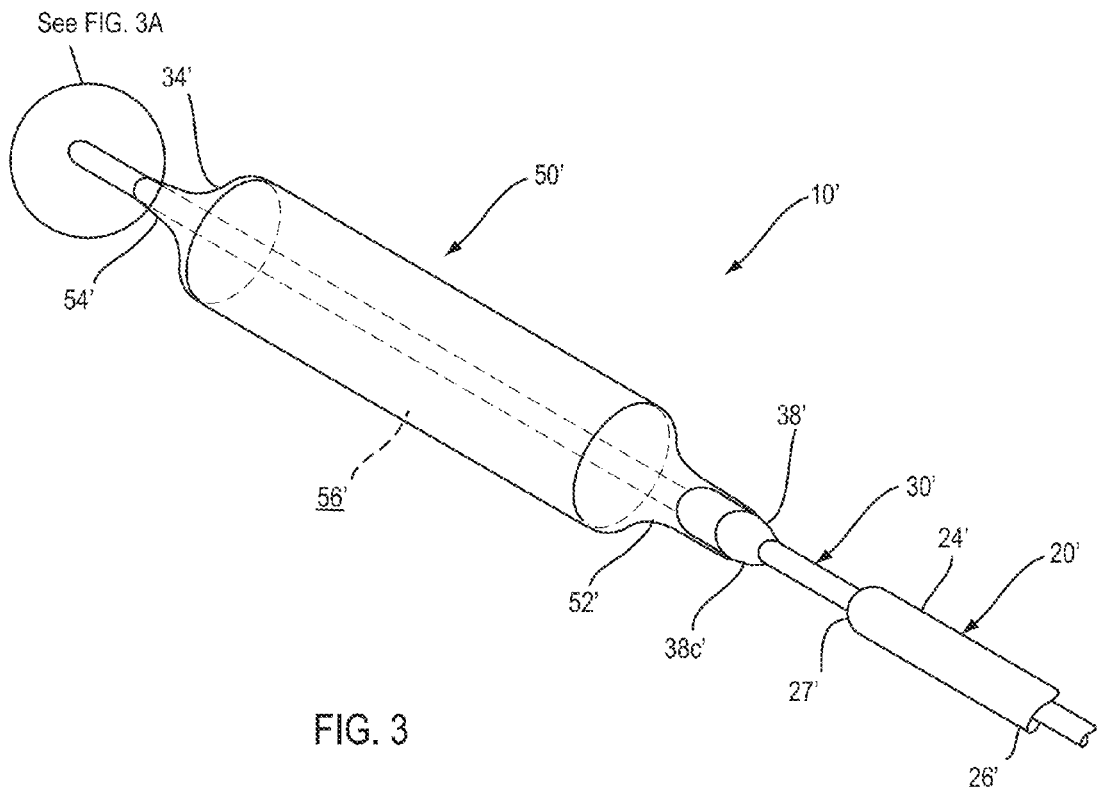
FIG. 3 is a perspective view of a distal end of another exemplary embodiment of an apparatus for treating a body lumen.
Figure 3A:
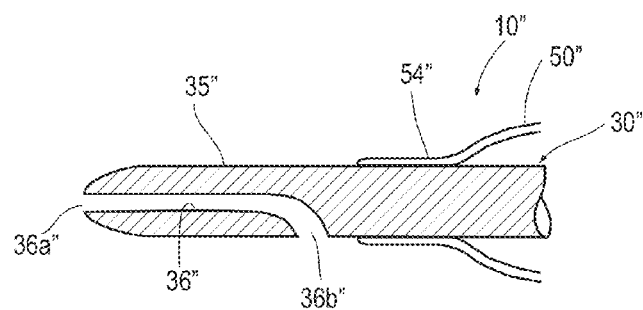
FIG. 3A is a detail of an optional distal tip including a relatively short guidewire lumen, which may be provided on the apparatus of FIG. 3.
Figure 4A:
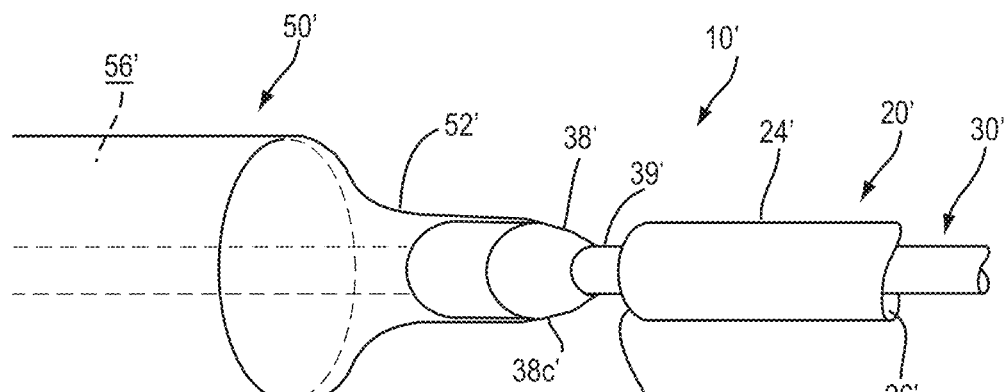
FIGS. 4A and 4B are details of the apparatus of FIG. 3 showing the valve in open and closed positions, respectively.
Figure 4B:
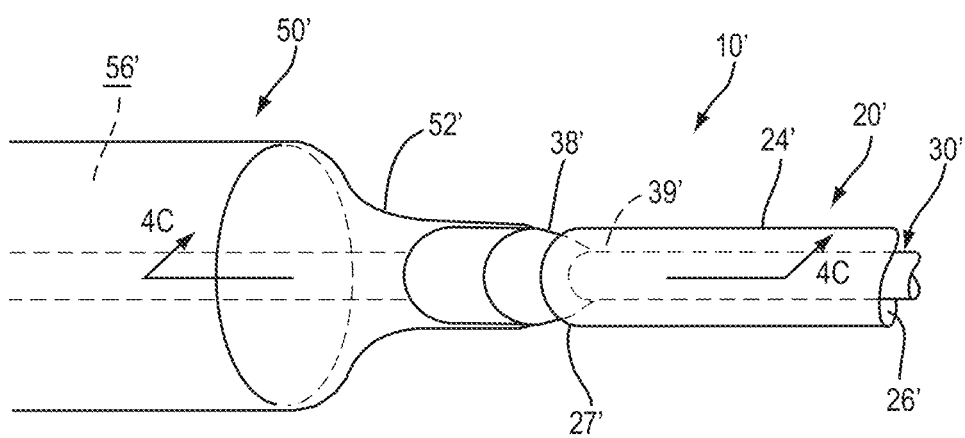
Figure 4C:
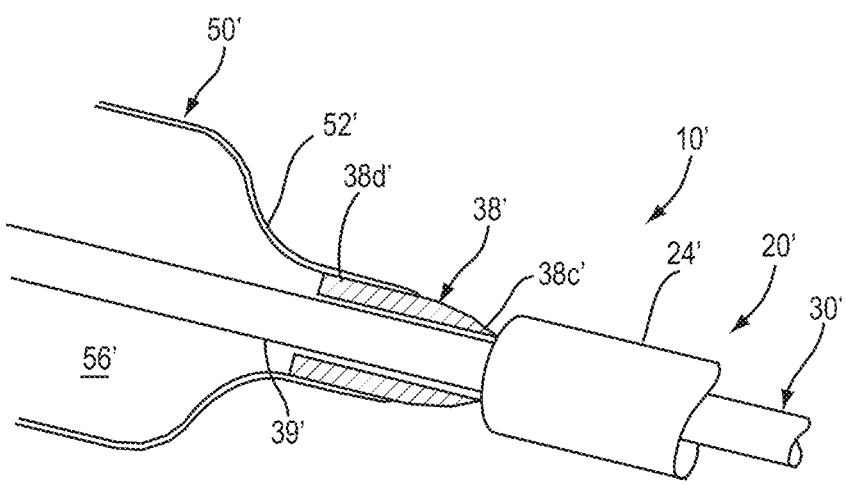
FIG. 4C is a cross-sectional view of the apparatus of FIGS. 3, 4A, and 4B taken along line 4C-4C of FIG. 4B.

Alternatively, as shown in FIGS. 3-4C, a sealing member 38' may be provided that has an outer diameter that is larger than the inner diameter of the outlet 27.' In this alternative, the sealing member 38' may also include a tapered proximal end 38c', e.g., to facilitate the sealing member 38' engaging or being received at least partially within the outlet 27' of the outer member 20.' Thus, only the tapered proximal end 38c' may be received within the outlet 27' until the larger midsection of the sealing member 38' abuts the distal end 24' of the outer member 20' to provide a substantially fluid-tight seal.

As best seen in FIGS. 2A and 2B, the sealing member 38 may include one or more passages 39 extending generally longitudinally between the proximal end 38c and a distal end 38d of the sealing member 38, e.g., a plurality of enclosed passages or grooves formed in the valve body 38a. For example, the valve body 38a may be formed as an extrusion including a bore for receiving the inner member 30 and one or more enclosed passages 39 extending between the ends 38c, 38d. Alternatively, enclosed lumens may be formed within the wall of the tubing to provide the passage(s) 39 using other methods. In a further alternative, shown in FIGS. 3-4C, the sealing member 38' may be provided as a length of tubing with one or more longitudinal grooves formed in an inner surface thereof. When the sealing member 38' is attached to or otherwise placed around the inner member 30,' the groove(s) may extend along the outer wall of the inner member 30,' thereby together defining the passage(s) 39.'

In addition or alternatively, if desired, the apparatus 10 may include one or more markers to facilitate positioning and/or advancement of the apparatus 10 during use. For example, as best seen in FIG. 1, radiopaque markers 29 may be provided on the distal portion 48 of the inner member 30, e.g., aligned with or adjacent the proximal and distal ends 52, 54 of the balloon 50.

In addition or alternatively, one or more radiopaque markers (not shown) may be provided on the outer member distal end 24, on the distal tip 35, on the balloon 50, e.g., on the proximal and/or distal ends 52, 54, and/or on the sealing member(s) 38. Alternatively, one or more components of the apparatus 10 may be formed from radiopaque or other materials that may facilitate imaging the apparatus 10 during use. For example, radiopaque markers and/or materials may facilitate positioning or otherwise imaging the apparatus 10 using fluoroscopy or other x-ray imaging, e.g., when positioning the balloon 50 (either before or after expansion) and/or when infusing fluid via the outlet 27. Alternatively, echogenic markers and/or materials may be provided to facilitate imaging using ultrasound or similar imaging techniques.

Returning to FIGS. 1-2B, during assembly, the sealing member 38 may be placed around the inner member 30 at the desired location on the distal end 34, e.g., proximal to the desired length for the distal portion 48 and attached thereto, e.g., by bonding with adhesive, sonic welding, fusing, heat shrinking, and the like. The proximal end 52 of the balloon 50 may then be positioned partially over the sealing member 38 and attached thereto. Thus, the passage(s) 39 may communicate from the outside of the proximal end 38c of the sealing member 38 with the interior 56 of the balloon 50. The distal tip 35 may be attached to the inner member 30, e.g., by an interference fit, bonding with adhesive, cooperating connectors, sonic welding, fusing, and the like. The distal end 54 of the balloon 50 may be attached to the distal end 34 of the inner member 30, e.g., closer to or over the distal tip 35. Consequently, the interior 56 of the balloon 50 may be substantially sealed other than the passage(s) 39 through the sealing member 38.

With additional reference to FIG. 1, the outer member 20 may be positioned around the inner member 30 and the handle 60 and actuator 62 may be coupled to the outer and inner members 20, 30, respectively, e.g., similar to embodiments disclosed in the applications incorporated by reference herein. The apparatus 10 may be operable in a first mode for delivering fluid into a body lumen (not shown) into which the apparatus 1010 is introduced (or otherwise exterior to the distal end 24 of the outer member 20) and a second mode for inflating the balloon 50.

For example, the inner member 30 may be movable between a first or distal position, shown in FIG. 2A, where the sealing member 38 is spaced apart from the outlet 27 of the outer member 20, and a second or proximal position, shown in FIG. 2B, where the sealing member 38 at least partially enters the outlet 27 and first lumen 26. In the first position, fluid delivered through the lumen 26 of the outer member 20 may exit the outlet 27 and enter the body lumen or other exterior environment, e.g., proximal to the distal portion 48. In the second position, the valve seal(s) 38b may substantially seal the outlet 27 such that fluid delivered through the lumen 26 may enter through the passage(s) 39 in the sealing member 38 and into the interior 56 of the balloon 50, thereby inflating the balloon 50. In addition, in the second position, a vacuum may be applied to the first lumen 26 to aspirate inflation media from the interior 56, e.g., to collapse the balloon 50 when desired.

Figure 5:
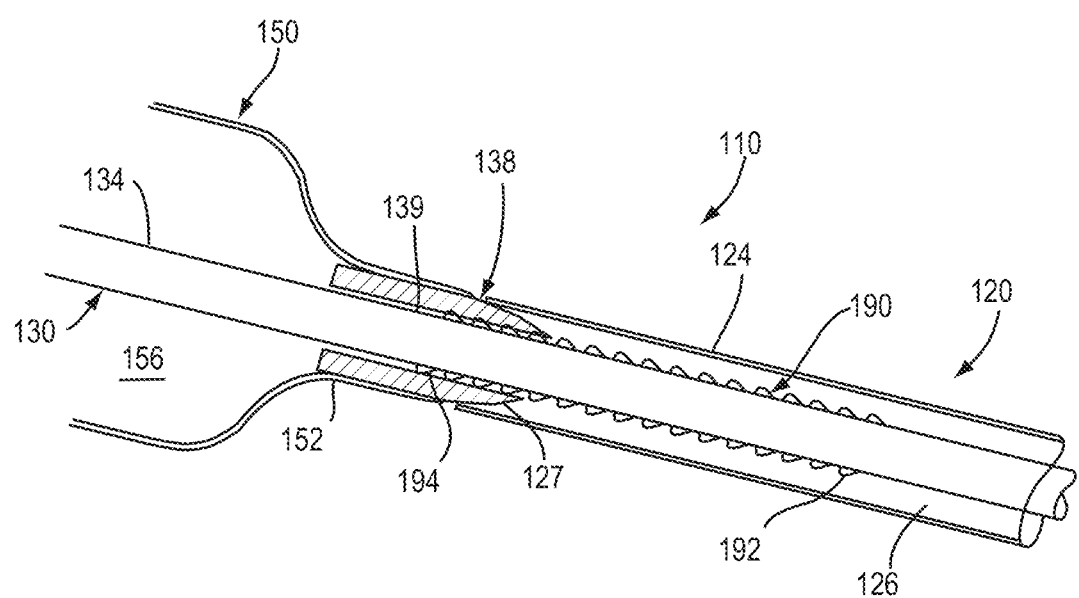
FIG. 5 is a cross-sectional view of an alternative embodiment of the apparatus of FIGS. 3 and 4A-4C.

Turning to FIG. 5, an alternative embodiment of the apparatus 110 is shown similar to the apparatus 10, 10' described above. The apparatus 110 includes an outer member 120, an inner member 130, a balloon 150, and a sealing member 138 similar to the apparatus 10, 10.' The apparatus 110 may be operable in first and second modes by directing the inner member 130 between a first or distal position and a second or proximal position, also similar to the apparatus 10, 10.'

However, unlike the previous embodiments, the apparatus 110 includes a spring or other biasing mechanism 190 coupled between the inner and outer members 130, 120 for biasing the inner member 130 to one of the first and second positions. For example, as shown, the spring 190 may bias the inner member 130 towards the proximal position, i.e., such that the outlet 127 of the apparatus 110 is normally closed and/or to enhance sealing the outlet 127 with the sealing member 138. The bias may be overcome by directing the inner member 130 distally to unseat the sealing member 138 and open the outlet 127.

As shown, the spring 190 includes a first end 192 attached or otherwise coupled to the distal end 124 of the outer member 120, and a second end 194 attached or otherwise coupled to the distal end 134 of the inner member 130 and/or the sealing member 138. For example, the second end 194 of the spring 190 may be attached between the sealing member 138 and the inner member 130 or otherwise to the sealing member 138, while still accommodating the passage 139 extending through the sealing member 138. In exemplary embodiments, the ends 192, 194 of the spring 190 may be attached to the inner and outer members 130, 120 by bonding with adhesive, sonic welding, fusing, interference fit, one or more connectors (not shown), and the like.

The relative diameter of the spring 190 and the inner member 130 may be set to reduce the risk of over-extension of the spring 190. For example, the spring 190 may be relaxed or under slight tension when the inner member 130 is in the proximal position and may be placed under higher tension when the inner member 130 is directed distally. As the spring 190 is placed under higher tension, the diameter of the spring 190 may decrease thereby increasing friction between the spring 190 and the inner member 130. This increasing friction may reduce the risk of over-extending the spring 190, which may otherwise plastically deform the spring 190 or otherwise prevent the spring 190 from subsequently biasing the inner member 130 proximally towards the proximal position.

Figure 6:
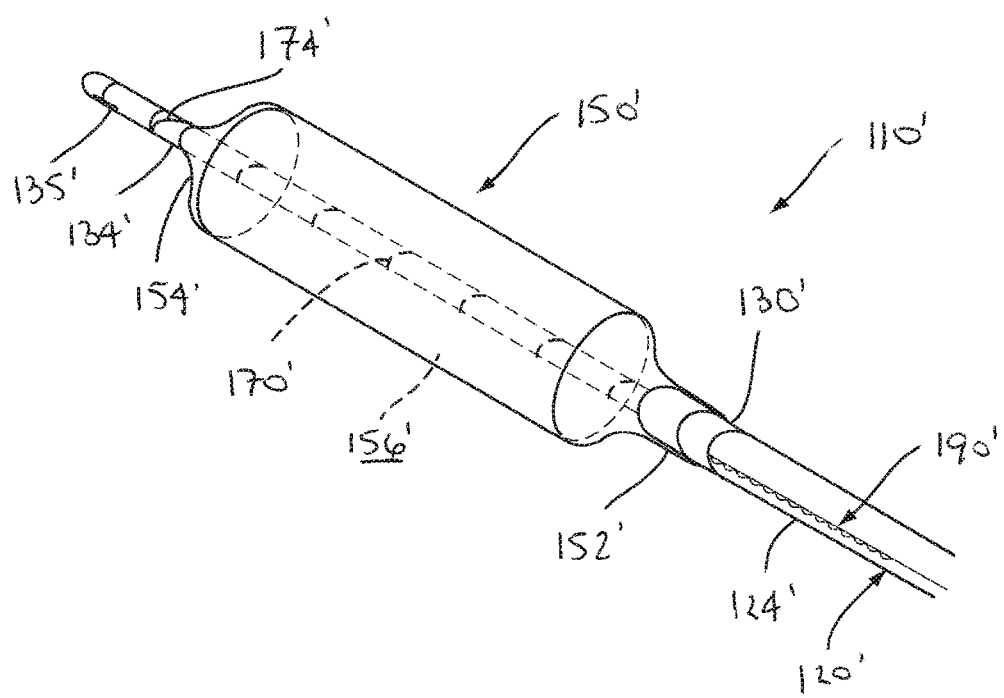
FIG. 6 is a perspective view of a distal end of yet another exemplary embodiment of an apparatus for treating a body lumen.

Turning to FIG. 6, yet another alternative embodiment of the apparatus 110' is shown similar to the apparatus 110 of FIG. 5. The apparatus 110' includes an outer member 120,' an inner member 130,' a balloon 150,' a sealing member 138,' and a spring 190,' similar to the apparatus 110. The apparatus 110' may be operable in first and second modes by directing the inner member 130' between a first or distal position and a second or proximal position, also similar to the apparatus 10, 10.'

In addition, the apparatus 110' includes a helical member 170' within the balloon 150' that may be expanded to an expanded helical shape, similar to embodiments in the applications incorporated by reference herein. For example, the helical member 170' may include a first or proximal end coupled to the outer member 120' (not shown) and a second or distal end 174' coupled to the inner member 130,' adjacent the distal end 154' of the balloon 150.' Thus, the apparatus 110' may also be operated in a third mode, e.g., by directing the inner member 130' proximally from the second position to a third position in which the helical member 170' is axially compressed and radially expanded. The balloon 150' may remain collapsed while the helical member 170' is expanded or may be inflated and then collapsed after the helical member 170' is expanded, similar to embodiments in the applications incorporated by reference herein.

After the helical member 170' and balloon 150' are used to remove material in the expanded helical shape, the inner member 130' may be directed distally to return the helical member 170' to its original contracted shape around the inner member 130.' This action may extend the spring 190' and open the outlet 127.' However, as discussed above, the relative sizes of the spring 190' and the inner member 130' may be such that the spring 190' compresses as it extends and frictionally engages the inner member 130,' thereby reducing the risk of the spring 190' over-extending while the inner member 130' is directed distally.

Turning to FIGS. 21A-22B, another embodiment of an apparatus 810 is shown, which may be similar to the apparatus 10, 10' described above (or one or more of features of the apparatus 810 may be incorporated into any of the embodiments described herein or in the applications incorporated by reference herein). The apparatus 810 generally includes an outer member 820 including proximal and distal ends 822, 824, an inner member 830 including proximal and distal ends 832, 834, a balloon 850 including proximal and distal ends 852, 854, and a sealing member 838 similar to the apparatus 10, 10.'

Figure 21A:
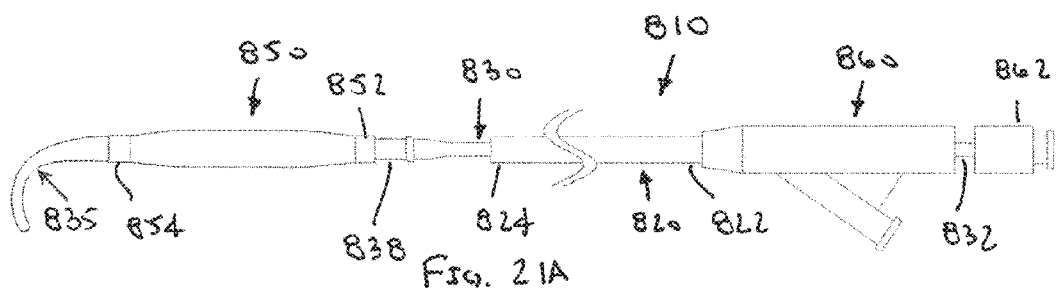
FIGS. 21A and 21B are side views of still another exemplary embodiment of an apparatus for treating a body lumen including a rotatable curved distal tip, showing the distal tip in first and second orientations.
Figure 21B:
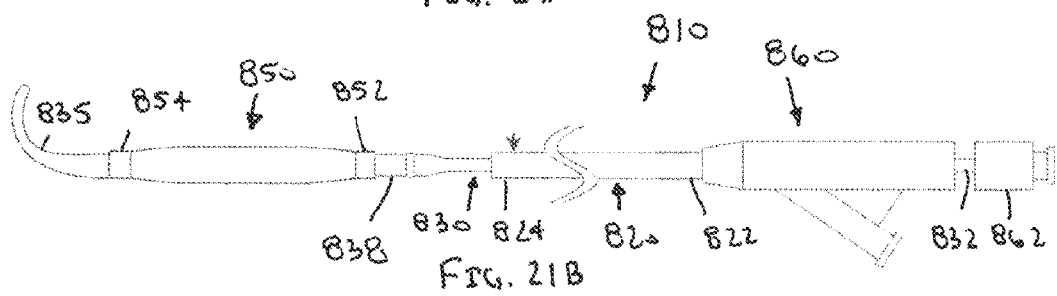
Figure 21C:
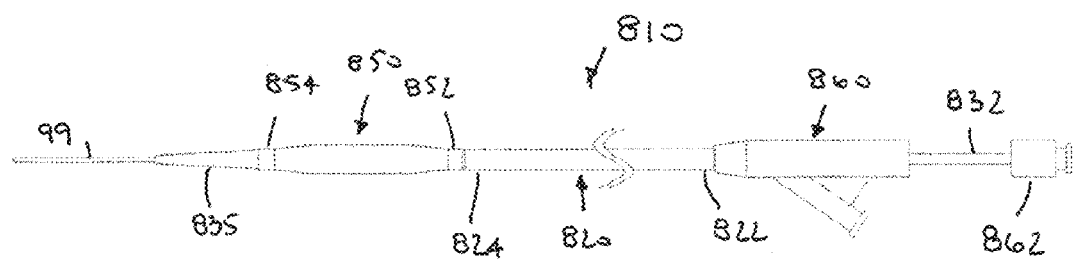
FIG. 21C is a side view of the apparatus of FIGS. 21A and 21B, showing a guidewire introduced through the apparatus to substantially straighten the distal tip.

The apparatus 810 also includes a flexible distal tip 835 extending from the distal end 834 of the inner member 830 that has a "J" tip or other curved shape. Optionally, the distal tip 835 may have a tapered shape that narrows distally from the balloon 850 or may have a substantially uniform cross-section (not shown), if desired. The distal tip 835 may be biased to the curved shape yet may be resiliently flexible such that the distal tip 835 may be at least partially straightened, e.g., by directing a guidewire or other rail 99 having greater rigidity than the distal tip 835 through the distal tip 835, as shown in FIG. 21C. Thus, with the guidewire 99 removed from the distal tip 835, the distal tip 835 may resiliently adopt its curved shape, as shown in FIGS. 21A and 21B, e.g., to facilitate advancement of the apparatus 810 through a patient's body. However, if desired, the distal tip 835 may be straightened, e.g., by introducing the guidewire 99 therethrough, to accommodate advancing the apparatus 810 over the guidewire 99, as shown in FIG. 21C.

The apparatus 810 may be operable in first and second modes by directing the inner member 830 between a first or distal position where the valve is open (see FIG. 22A), and a second or proximal position (see FIG. 22B) where the valve is closed, similar to other embodiments herein. For example, a handle 860 may be provided on the proximal end 822 of the outer member, and an actuator 862 may be coupled to the proximal end 832 of the inner member 830, similar to other embodiments herein. The actuator 862 may be movable axially, i.e., proximally and distally relative to the handle 860 for directing the inner member 830 between the proximal and distal positions.

In addition, unlike the previous embodiments, the actuator 862 and inner member 830 may be rotatable about a longitudinal axis of the apparatus 810. Thus, the actuator 862 may be rotated relative to the handle 860 to rotate the inner member 830 and thereby change the orientation of the curved distal tip 835. For example, FIGS. 21A and 21B show the curved distal tip 835 in opposite orientations, which may be achieved by rotating the actuator 862 about one hundred eighty degrees (180°) relative to the handle 860. Thus, rather than rotating the entire apparatus 810, i.e., including both the outer and inner members 820, 830 to change the orientation of the distal tip 835, only the inner member 830 need be rotated. If the entire apparatus 810 were rotated, the outer member 820 may become twisted or otherwise fail to transmit substantial torque between its proximal and distal ends 822, 824, e.g., if the outer member 820 is formed from polymeric material having poor torque transmission. Instead, the inner member 830 may be decoupled from the outer member 820, i.e., freely rotatable therein, thereby facilitating transmitting torque freely between the proximal and distal ends 832, 834.

To facilitate transmission of such rotation between the proximal and distal ends 832, 834 of the inner member 830, the shaft of the inner member 830 may be formed from a composite or other construction that resists twisting. For example, the inner member 830 may be formed from a stainless steel (or other metal or polymeric strong fiber) braid in a polymeric matrix (e.g., a thermoset polymeric matrix, such as polyimide, that resists the inner member 830 taking a shape set when bent or curved). Such construction may provide good flexibility while also maintaining substantial torque transmission between the proximal and distal ends 832, 834.

The actuator 862 may be freely rotatable relative to the handle 860, if desired. Alternatively, cooperating features (not shown) may be provided, e.g., on the handle 860 and inner member 830, to limit rotation of the actuator 862 and inner member 830. For example, one or more detents or tracks (not shown) may be provided within the handle 860 and/or on the proximal end 832 of the inner member 830 that interact to limit rotation to less than three hundred sixty degrees (360°). Thus, a user may be able to rotate the actuator 862 to change the orientation of the curved distal tip 835 close to a complete rotation, while limiting excessive rotation in one direction, which may otherwise apply excessive torque on the inner member 830.

To allow rotation of the inner member 830 relative to the outer member 820, the actuator 862 may be directed to the first position, thereby opening the valve and decoupling the distal end 824 of the outer member 820 from the sealing member 838 and, consequently, from the inner member 830. In the first position, the inner member 830 may be rotated relative to outer member 820 to change the orientation of the distal tip 835.

Optionally, the sealing member 838 and/or outer member 820 may be constructed to minimize friction therebetween, e.g., to allow rotation of the inner member 830 in the second position with the valve closed. In this option, materials having a relatively low coefficient of friction, e.g., PTFE, polyethylene, and the like, may be provided, e.g., on the outer surface of the sealing member 838 and/or on the inner surface of the distal end 824 of the outer member 820. Thus, rather than having to open the valve to decouple the outer and inner members 820, 830, the members may freely rotate relative to one another even with the valve closed.

Returning to FIGS. 1-2B, the apparatus 10 (or any of the embodiments herein) may be introduced into a body lumen (not shown), e.g., via a patient's vasculature or other natural or surgically created passages, to perform one or more therapeutic and/or diagnostic medical procedures. In an exemplary embodiment, the target body lumen may be a blood vessel, e.g., a vein or artery, a graft, e.g., an aorto-venous fistula, tubular xenograft, or synthetic tubular graft, and the like. For example, the body lumen may be a passage communicating between an adjacent artery and vein (not shown), e.g., in an arm or other region of a dialysis patient. Alternatively, the body lumen may be a blood vessel within a patient's vasculature, e.g., a peripheral vessel in a patient's leg, a cerebral vessel, and the like. In a further alternative, the material may be a stone within a patient's urinary tract or other foreign object to be removed from the patient's body. In yet another alternative, the body lumen may be an aorta or a chamber of a heart, e.g., the site of a heart valve in need of repair, replacement, or other treatment.

Optionally, the body lumen may be accessed using one or more additional instruments (not shown), which may be part of a system or kit including the apparatus 10. For example, an introducer sheath, guide catheter, or other tubular member (not shown) may be introduced adjacent the target treatment site where material is to be removed, or may be introduced elsewhere in the patient's body to provide access to the patient's vasculature or other passages communicating with the body lumen. If the body lumen is located in a peripheral vessel of the patient's vasculature, a percutaneous puncture or cut-down may be created using a needle or other instrument (not shown) at a peripheral location, such as a femoral artery, carotid artery, or other entry site (also not shown), and an introducer sheath may be placed through the puncture at the peripheral location to provide access. The apparatus 10 may be advanced through the patient's vasculature from the entry site, e.g., alone or with the aid of a guide catheter, guidewire, and the like (not shown).

For example, to facilitate directing the apparatus 10 from an entry site to the target body lumen, a guide catheter, microcatheter, or other tubular body may be placed from the entry site to the body lumen using conventional methods. In addition or alternatively, a guidewire (not shown) may be placed from the entry site to the body lumen if desired, e.g., if the inner member 30 includes the second lumen 36. Alternatively, if the apparatus 10 includes a rapid-exchange guidewire lumen in its distal tip, the guidewire may be backloaded through the distal tip to facilitate advancing the apparatus 10 along the guidewire. Optionally, the guide catheter or tubular body may also be used for aspiration, e.g., coupled to a source of vacuum for capturing material removed by the apparatus 10, as described further below and in the applications incorporated by reference herein.

Initially, with reference to FIG. 2A, the apparatus 10 may be provided with the inner member 30 in the second position and the sealing member 38 substantially sealing the outlet 27. In this position, the sealing member 38 may also provide a substantially smooth transition for the distal end 24 of the outer member 20 (in addition to sealing the outlet 27), e.g., which may facilitate advancement of the apparatus 10 with minimal risk of damaging the walls of body lumens, e.g., when the apparatus 10 is advanced through tortuous anatomy. Alternatively, the apparatus 10 may be introduced with the inner member 30 in the first position, i.e., with the outlet 27 open, if desired, to facilitate delivery of fluids during manipulation of the apparatus 10.

If the apparatus 10 includes a curved distal tip (not shown), e.g., similar to the apparatus 810 shown in FIGS. 21A-22B, the distal tip may be straightened during advancement over a guidewire or other rail. If desired to deploy the distal tip in its curved shape, the guidewire may be withdrawn partially until removed from the distal tip, whereupon the distal tip may resiliently return to its curved shape. The curved tip may then be rotated, e.g., by rotating the inner member if the inner member is rotatable independent of the outer member or the entire apparatus 10, to access a branch or otherwise facilitate advancement of the apparatus 10 from one body lumen into another. For example, once the curved tip is rotated and the apparatus manipulated sufficiently within a body lumen, e.g., to advance the distal tip into a branch adjacent the body lumen, the guidewire may be advanced again to straighten the distal tip and advance the guidewire before advancing the apparatus 10 further.

At any time, if it is desired to deliver fluid into the body lumen, the inner member 30 may be directed to (if not already in) the distal or first position to space the sealing member 38 from the distal end 24 of the outer member 20 and open the outlet 27 (FIG. 2A). Fluid may then be delivered through the lumen 26 of the outer member and out the outlet 27 into the body lumen. Because the outlet 27 is spaced away from the sealing member 38, substantially all of the fluid is injected into the body lumen and does not pass through the passage(s) 39 into the balloon 50.

For example, radiopaque contrast or other fluid may be delivered into the body lumen via the annular passage defined by the first lumen 26 between the outer and inner members 20, 30 to facilitate monitoring and/or identifying the location of the distal portion 48 and/or a target treatment site. Markers 29 (and/or other markers, not shown) on the apparatus 10 may facilitate positioning the balloon 50 relative to the treatment site. For example, contrast may facilitate identifying obstructive material intended to be dilated or removed within a body lumen, an implantation site for a prosthesis, and the like before the balloon 50 is expanded, e.g., to facilitate verifying that the balloon 50 is positioned within or adjacent the treatment site.

As best seen in FIG. 2B, when it is desired to expand the balloon 50 (and/or otherwise perform a procedure involving another treatment element, not shown, on the distal portion 48), the inner member 30 may be directed to (or may be automatically biased to) the proximal or second position, e.g., to substantially seal the outlet 27 with the sealing member 38 (FIG. 2B). The sealing member 38 may provide a substantially fluid-tight seal of the outlet 27 such that subsequent fluid delivery through the first lumen 26 causes the fluid to pass through the passage(s) 39 of the sealing member 38 into the interior 56 of the balloon 50, thereby inflating the balloon 50.

For example, during an exemplary procedure, the apparatus 10 may be positioned until the distal portion 48 and balloon 50 are positioned distally beyond an obstructed region within a body lumen. With the inner member 30 in the second position sealing the outlet 27, the balloon 50 may be inflated within the body lumen, e.g., such that the balloon 50 extends substantially entirely across the body lumen. The entire apparatus 10 may then be retracted to pull the material from the body lumen, e.g., to be aspirated into a guide catheter (not shown), or otherwise removed from the body lumen. Optionally, the balloon 50 may be directable to a helical configuration, similar to the apparatus in the applications incorporated by reference herein, e.g., to facilitate removal of material within the body lumen.

Once material is removed, the inner member 30 may be directed back towards the second position, and fluid may be introduced through the outlet 27 to observe the amount of material removed and/or remaining within the body lumen. If additional material is to be removed, the inner member 30 may be directed to the first position, e.g., if desired to advance the apparatus 10 through additional material to be removed. Once the balloon 50 is located beyond the material, the process may be repeated as often as desired with the valve opened and closed to monitor the position of the balloon 50 and/or progress of removal.

In addition, if desired, the obstructive material may be treated, e.g., at least partially dissolved, macerated, and the like before, during, or after withdrawal. For example, a therapeutic agent may be delivered into the body lumen via the first lumen 26 and outlet 27 of the outer member 20, e.g., to at least partially dissolve or separate thrombus or other relatively soft material before being removed by the balloon 50 and/or otherwise to treat the wall of the body lumen.

To collapse the balloon 50, e.g., after inflating the balloon 50 to remove material, dilate an obstruction, and/or otherwise treat a body lumen, fluid may be evacuated from the interior 56 through the passage(s) 39 and the first lumen 26. Alternatively, the inner member 30 may be directed towards the first position to disengage the sealing member 38 and open the outlet 27. The fluid within the balloon 50 may then be free to escape through the passage(s) 39 into the body lumen and deflate the balloon 50 without requiring aspiration.

Optionally, if desired, the inner member 30 may be positioned at an intermediate position, i.e., between the first and second positions, e.g., as shown in FIG. 15B, in which fluid delivered from the outlet 27 may be divided such that some fluid enters the passage(s) 39 and expands the balloon 50 while the remaining fluid is delivered into the body lumen, as described further below. The relative amount of inflation and fluid delivery into the body lumen may be adjusted, as desired, simply by directing the inner member 30 proximally or distally to move the sealing member 38 closer to or further from the outlet 27. This procedure may be accomplished using external imaging, e.g., if the fluid includes radiopaque contrast, to monitor the inflation and/or position of the balloon 50 and/or the surrounding vasculature within which the balloon 50 is located.

In another option, the apparatus 10 may be used to deliver and aspirate fluid using the outlet 27. For example, a user may want to deliver and remove one or more diagnostic and/or therapeutic agents within a body lumen using the apparatus 10. In one example, contrast, dyes, or other material for facilitating imaging may be delivered into the body lumen from the outlet 27 (with the inner member 30 and sealing member 38 in the first position) and then aspirated back into the outlet 27 to reduce the amount of contrast that remains within the body lumen or travels to other locations in the patient's body. In addition or alternatively, the outer member 20 may include one or more additional lumens (not shown, see, e.g., FIG. 14B) extending between the proximal and distal ends 22, 24, if desired, e.g., for delivering and/or aspirating material into/from an exterior environment adjacent the distal end 24.

In another example, a lytic agent may be delivered into the body lumen, e.g., to break up clot or other material within the body lumen, and then loose material may then be aspirated into the outlet 27 and through the lumen 26 (or into a guide catheter, not shown, positioned over the apparatus 10), which may reduce the risk of bleeding or otherwise exposing the lytic agent systemically to the patient's body. The outlet 27 may also be used to aspirate pieces of thrombus or other material that is not dissolved or broken down by the agent and/or is otherwise loosened within the body lumen. During such procedures, the balloon 50 may be at least partially inflated, e.g., by directing the inner member 30 to an intermediate position, as shown in FIG. 15B, to stop or reduce flow through the body lumen while the one or more agents are delivered and aspirated, which may also reduce exposure of other locations to the agent(s) delivered into the body lumen.

With the apparatus 10 and procedures described herein, the first lumen 26 may be used for both inflation of the balloon 50 and delivering fluid into the body lumen. Thus, the profile of the outer member 20 and therefore of the overall apparatus 10 may be smaller than devices that include separate inflation and infusion lumens. Further, although the second lumen 36 of the inner member 30 could be used for infusion of fluids, this would generally require removing the guidewire over which the apparatus 10 is introduced since the guidewire may substantially fill the second lumen 36. Because the first lumen 26 may be used for infusion, the guidewire may remain within the second lumen 36 throughout the procedure, thereby potentially reducing the number of guidewire or other device exchanges. Further, the apparatus 10 may remain over the guidewire, which may facilitate advancing the apparatus 10 to other target body lumens intended for treatment, as explained in the applications incorporated by reference herein.

Figure 16A:
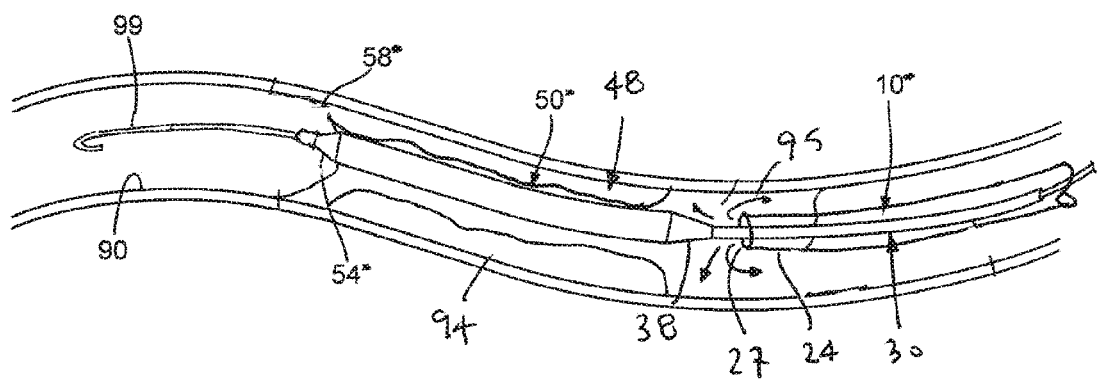
FIGS. 16A-16C are cross-sectional views of a body lumen within a patient's body showing different methods for treating a body lumen using the apparatus herein.

Turning to FIG. 16A, in another exemplary method, the body lumen 90 may include an occlusion 94, e.g., a partial or chronic total occlusion within a blood vessel, and the apparatus 10 may be introduced to dilate and/or otherwise treat the occlusion 94. As shown, a guidewire 99 has been tracked from an entry site (not shown) into the body lumen 90 and through the occlusion 94, e.g., using known methods. Chronic total lesions may be particularly difficult to treat because there is little opportunity to perform conventional dye injections to facilitate imaging since there is no flow through the body lumen 90. Further, it may be difficult to track and/or position the guidewire 99 and/or apparatus 10 within the body lumen 90 without using dye injections.

Initially, the apparatus 10 may be advanced into the body lumen 90 with the balloon 50 in its collapsed condition. For example, the apparatus 10 may be advanced over the guidewire 99 previously placed through the occlusion 94, e.g., until the distal end 54 of the balloon 50 enters the region of the body lumen 90 beyond the occlusion 94, as shown. With the balloon 50 positioned at least partially within the occlusion 94, the inner member 30 may be directed to open the outlet 27, and radiopaque contrast, dye, or other fluid (represented by 95) may be delivered into the body lumen 90 via the annular passage defined by the first lumen 26 between the outer and inner members 20, 30 to facilitate locating and/or measuring the size of the material of the occlusion 94 and/or body lumen 90, e.g., using fluoroscopy. Markers 29 (not shown in FIG. 16A, see FIG. 1) on the apparatus 10 may facilitate positioning the balloon 50 relative to the occlusion 94 before the balloon 50 is expanded, e.g., to facilitate verifying that the balloon 50 is positioned through and/or across the occlusion 94. If desired, the inner member 30 may be directed back and forth between the first and second positions, e.g., to allow infusion of contrast and inflation of the balloon 50 to dilate the occlusion 94 and monitor the progress of the treatment.

Thus, the apparatus 10 may facilitate dye injection adjacent the occlusion 94 while maintaining the guidewire 99 in position. Unlike the apparatus 10, conventional devices may require removing a guidewire or other device advanced through the occlusion 94 to allow dye injections and imaging around the occlusion 94. In such procedures, it may be difficult to reintroduce the guidewire or other device back through the small passage created through the occlusion 94.

If desired, obstructive material may be treated, e.g., at least partially dissolved, macerated, and the like before, during, or after withdrawal. For example, a therapeutic agent may be delivered into the body lumen 90 via the first lumen 26 and outlet 27 of the outer member 20, e.g., to at least partially dissolve or separate thrombus or other relatively soft material before being dilated by the balloon 50. In addition or alternatively, the distal portion 48 may carry one or more other treatment elements, e.g., an abrasive tip, a passive or active atherectomy tool, and the like (not shown), in addition to or instead of the balloon 50. Exemplary tips and methods for using them are disclosed in application Ser. No. 12/966,925, filed Dec. 13, 2010, the entire disclosure of which is expressly incorporated by reference herein.

Figure 16B:
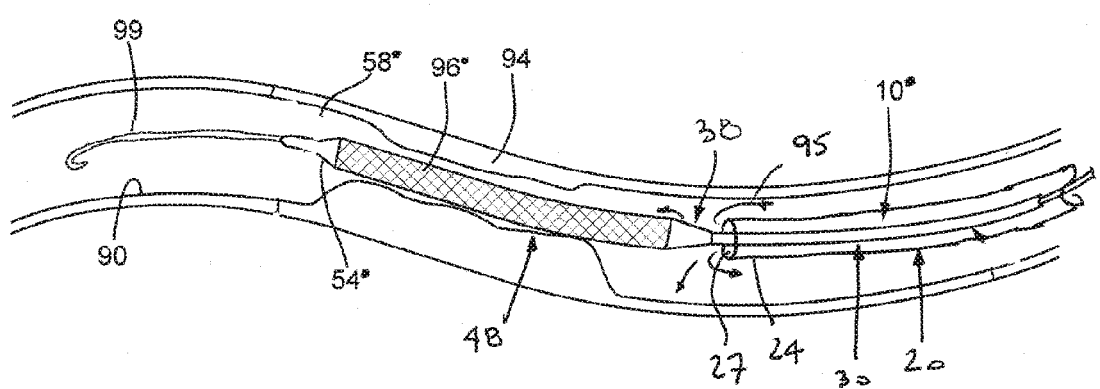

Optionally, as shown in FIG. 16B, a stent 96 may be carried by the balloon 50 and may be expanded by inflating the balloon 50. For example, with the valve of the apparatus 10 open, dye 95 may be injected into the body lumen 90 to facilitate imaging and positioning the apparatus 10. Once the stent 96 is positioned across the occlusion 94, the valve may be closed, and the balloon 50 may be inflated to expand the stent 96 and dilate the occlusion 94 (not shown). Once the stent 96 is expanded, the balloon 50 may be collapsed and the apparatus 10 removed from the body lumen 90 and patient's body.

Alternatively, the apparatus 10 may be used to introduce and/or deploy other prostheses instead of or in addition to the stent 96. For example, a tubular stent-graft, one or more components of a prosthetic valve, and the like (not shown) may be carried by the distal portion 48, e.g., over the balloon 50. The prosthesis may be expanded or otherwise deployed within a body lumen, e.g., by inflating the balloon 50, as described above, with fluid being selectively introduced, as desired.

Figure 16C:
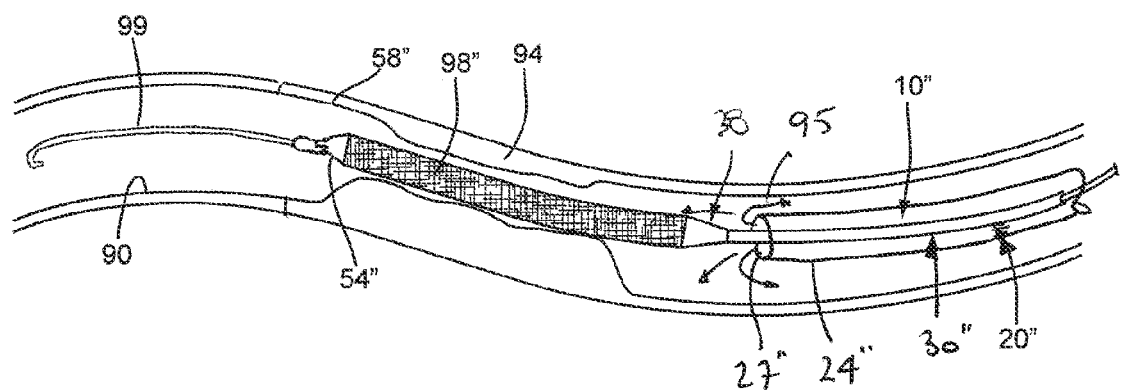

Turning to FIG. 16C, in another method, the apparatus 10" may be used as a drug delivery platform for treating the occlusion 94. For example, in some applications, it may be desirable to deliver an anti-restenosis drug without a stent. As shown, the apparatus 10" includes a carrier 98" provided over the balloon 50" that may be delivered into the body lumen 90 and/or through the occlusion 94." For example, similar to the methods described above, the apparatus 10" may be advanced into the body lumen 90 with the balloon 50" and the carrier 98" thereon in a collapsed condition, e.g., over the guidewire 99.

With the balloon 50" positioned within the occlusion 94 and the valve open, contrast, dye, or other fluid 95 may be delivered from the outlet 27" into the body lumen 90 to facilitate locating and/or measuring the size of the occlusion 94 and/or body lumen 90, e.g., using fluoroscopy. Once the apparatus 10" is positioned with the balloon 50" across the occlusion 94, the valve may be closed and the balloon 50" inflated within the body lumen 90 to dilate the occlusion 94 and deliver the carrier 98." Once the carrier 98" is delivered, the balloon 50" may be collapsed and the apparatus 10" removed from the body lumen 90 and patient's body. One or more therapeutic agents may be positioned within or otherwise carried by the carrier 98" and, therefore, may remain within the dilated occlusion 94 to treat the body lumen 90.

Alternatively, the agent(s) may be delivered directly from the wall of the balloon 50." For example, the agent(s) may be infused through the wall of the balloon 50," e.g., by providing a porous layer on the balloon 50" into which the agent(s) may be embedded or otherwise placed. In another alternative, the agent delivered into the body lumen 90 may be provided from multiple components that may react or interact in situ once delivered together within the body lumen 90. For example, a first component (or one or more additional components less than all components of the agent) may be carried on the wall of the balloon 50," e.g., in a porous layer or on a carrier 98" disposed around the balloon 50," as described above. The second component (or multiple remaining components needed for the agent) may be delivered via the outlet 27" on the apparatus 10." For example, after one or more components are delivered by closing the valve and inflating the balloon 50" within the occlusion 94, the valve may be opened and a fluid carrying the one or more remaining components may be delivered into the body lumen 90. The components may then combine to form an active drug or agent that may treat the material of the occlusion 94 and/or otherwise treat the body lumen 90.

In another alternative, a balloon (not shown) may be provided on the distal end 24 of the outer member 20 or on the distal portion 48 of the inner member 30 distal to the balloon 50, if desired, similar to embodiments in the applications incorporated by reference herein. Such a balloon may be a non-compliant, high pressure balloon, e.g., for dilating the body lumen, or an elastic, compliant balloon for substantially sealing the body lumen to isolate one or more regions of the body lumen before infusion of fluid therein. In such alternatives, the outer and/or inner members 20, 30 may include one or more additional lumens, e.g., as shown in FIGS. 14A-14C, providing inflation lumens for such additional balloons.

Turning to FIGS. 7A-7C, another embodiment of an apparatus 210 is shown that includes a tubular outer member 220, an elongate inner member 230, and a distal portion 248 carrying a treatment element, e.g., a stent or other prosthesis 296 covered by a cover or other constraint 298. Generally, the apparatus 210 may be operable in multiple modes, e.g., first and second modes, by directing the inner member 230 between a first or distal position and a second or proximal position for opening and closing a valve adjacent the distal portion 248, similar to other embodiments herein. In addition, the apparatus 210 may be operable for deploying the prosthesis carried on the distal portion 248, as described further below.

The outer member 220 includes a proximal end 222 coupled to a handle 260, a distal end 224 sized for introduction into a body lumen, and a first lumen 226 extending between the proximal end 222 and an outlet 227 in the distal end 224. The inner member 230 also includes a proximal end 232, a distal end 234, and, optionally, may include a second lumen 236 extending between the proximal end 232 and a distal tip 235. In addition, the inner member 230 may include an actuator member (not shown), e.g., slidably disposed within an actuator lumen (also not shown), coupled with the constraint 298 for selectively actuating the constraint 298, e.g., advancing the constraint distally or otherwise to deploy the prosthesis 296, as described further below.

The inner member 230 may have a length relative to the outer member 220 such that the inner member proximal end 230 is coupled to an actuator 264 on the handle 260, and the inner member distal end 234 extends distally beyond the outlet 227 of the outer member 220, e.g., to define the distal portion 248. The actuator 260 may be coupled to the proximal end 232 of the inner member 230 for directing the inner member 230 axially relative to the outer member 220, e.g., to open or close the outlet 227 and/or to direct the apparatus 210 between the different modes, similar to other embodiments herein.

Unlike the previous embodiments, the distal portion 248 includes the prosthesis 296 and constraint 298 adjacent a tapered proximal portion 238, extending at least partially between the proximal portion 238 and the distal tip 235. The tapered portion 238 may taper outwardly and distally from the inner member 230 to define an outer diameter similar to or larger than the outlet 227 of the outer member 220, e.g., to provide a sealing member for selectively sealing the outlet 227, similar to other embodiments herein. The tapered portion 238 may be formed from material similar to the rest of the distal portion 248, or the tapered portion 238 may be formed from flexible and/or resilient material to enhance the seal with the outlet 227.

The inner member 230 may be movable between a first or distal position, shown in FIG. 7B, where the outlet 227 is spaced apart from the proximal portion 238, and a second or proximal position, shown in FIG. 7A, where the tapered portion 238 engages the outlet 227 to substantially seal the outlet 227. For example, the actuator 262 may be directed between distal and proximal positions on the handle 260 to open and close the outlet 227, as shown, e.g., to allow fluid to be delivered from the first lumen 226 through the outlet 227 into a body lumen or other region adjacent the distal portion 248.

The distal portion 248 may have an outer diameter similar to the maximum diameter of the tapered portion 238, e.g., a substantially uniform diameter between the tapered portion 238 and the distal tip 235. Alternatively, the distal portion 248 may step down from the tapered portion 238, e.g., to accommodate receiving the prosthesis 296 thereon.

As shown, the constraint 298 may be movable from a first position overlying the stent 296 and a second position for exposing the stent 296. As best seen in FIG. 7C, an actuator 266 on the handle 260 may be advanced distally to direct an actuator member (not shown) in the inner member 330 and consequently the constraint 298 distally to expose the stent 296. In the embodiment shown, the stent 296 may be self-expanding, i.e., biased to expand to a diameter larger than a body lumen within which the stent 296 is intended to be deployed. Thus, as the constraint 298 is advanced, the stent 296 may resiliently expand as it is exposed until the constraint 298 is advanced sufficiently to expose the entire stent 296. Alternatively, other constraints may be provided instead of the sleeve 298 shown, e.g., one or filaments or elements (not shown) that may surround the stent 296 and/or secure the stent 296 on the distal portion 248 in a constrained state, yet may be withdrawn to release the stent 296 from the constrained state and allow the stent 296 to resiliently expand to a deployed state.

In addition or alternatively, a balloon or other expandable member (not shown) may be provided on the distal portion 248, e.g., underlying the stent 296. In this embodiment, the balloon may be inflated, e.g., by delivering fluid through the first lumen 266 with the inner member 230 in the second position such that the fluid passes through the outlet 227 and one or more passages (not shown) in the tapered portion 238 into an interior of the balloon. For example, the balloon may be inflated to plastically or otherwise further expand the stent 296 after deployment and/or dilate the body lumen within which the stent 296 is deployed.

In a further alternative, the stent 296 may be plastically expandable, e.g., similar to the embodiments described elsewhere herein. In this alternative, the constraint 298 may still be provided, if it is desired to protect the stent 296 (or other prosthesis) and/or provide a transition over the distal portion 248. Alternatively, the constraint 298 may be omitted and the stent 296 may be maintained on the distal portion 248, e.g., by compressing the stent 296 or by the stent 296 having a substantially relaxed state corresponding to the constrained state. In this alternative, a balloon or other expandable member (not shown) may be provided on the distal portion 248 to expand the stent 296, similar to other embodiments herein.

Figure 8A:
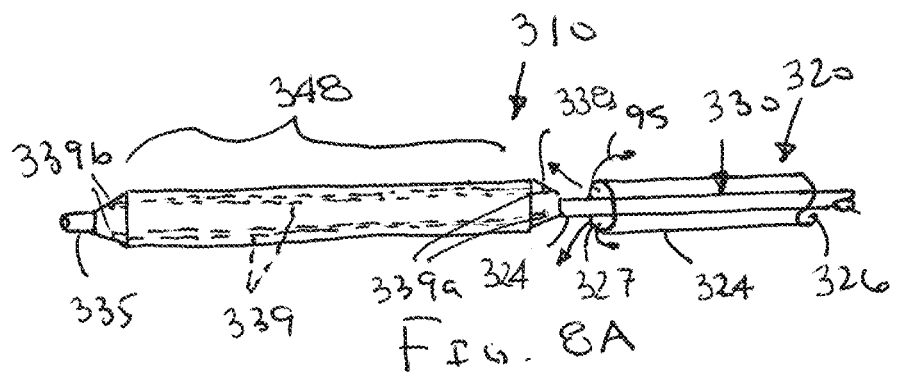
FIGS. 8A and 8B are side views of yet another exemplary embodiment of an apparatus operable in a first mode for infusing fluid into a body lumen proximal to a distal portion of the apparatus (FIG. 8A) and a second mode for delivering fluid into the body lumen distal to the distal portion (FIG. 8B).
Figure 8B:
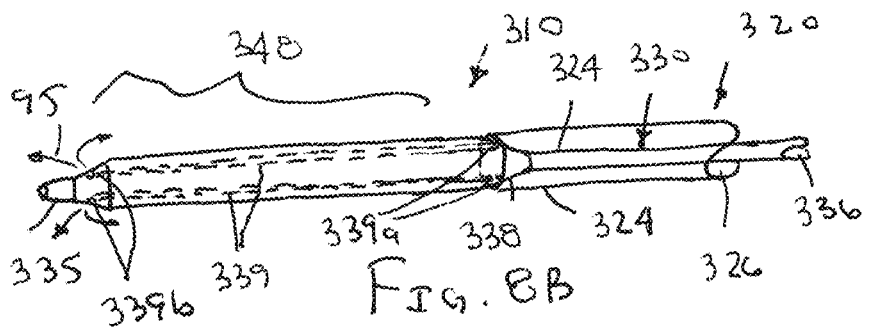

Turning to FIGS. 8A and 8B, another embodiment of an apparatus 310 is shown that includes a tubular outer member 320, an elongate inner member 330, and a distal portion 348, which may carry a treatment element, e.g., a balloon, stent or other prosthesis, and the like (not shown). The outer member 320 includes a proximal end coupled to a handle (not shown), a distal end 324 sized for introduction into a body lumen, and a first lumen 326 extending between the proximal end and an outlet 827 in the distal end 324.

The inner member 330 also includes a proximal end (not shown), a distal end 334, and, optionally, may include a second lumen 336 extending between the proximal end and a distal tip 335. The inner member 330 may be coupled to an actuator (not shown) on the handle, e.g., for directing the inner member 330 between a first or distal position, shown in FIG. 8A, and a second or proximal position, shown in FIG. 8B, for opening and closing a valve adjacent the distal portion 348.

For example, as shown, the distal portion 348 may extend from a tapered proximal portion 338 to the distal tip 335. Similar to the apparatus 210 shown in FIGS. 7A-7C, the tapered portion 338 may taper outwardly and distally from the inner member 330 to define an outer diameter similar to or larger than the outlet 327 of the outer member 320, e.g., to provide a sealing member for selectively sealing the outlet 327, similar to other embodiments herein. The tapered portion 338 may be formed from material similar to the rest of the distal portion 348, or the tapered portion 338 may be formed from flexible and/or resilient material to enhance the seal with the outlet 327. Alternatively, a separate sealing member (not shown) may be formed on or attached to the distal end 334 of the inner member 330, e.g., similar to the sealing members 38, 38' described previously. In this alternative, the distal portion 348 may have a diameter similar to other portions of the inner member 330.

As shown, the distal portion 348 may include one or more passages 339 extending at least partially along a length thereof, e.g., from one or more proximal ports 339a in the tapered portion 338 to one or more respective distal ports 339b in the distal portion, e.g., adjacent the distal tip 335. Optionally, the distal portion 348 may include a balloon or other expandable member (not shown), a stent or other prosthesis, and/or other treatment elements, similar to previous embodiments. For example, a balloon may be attached to the distal end 334 of the inner member 330 such that an interior of the balloon communicates with an inflation lumen (not shown) in the inner member 330, which may be the lumen 336 or a separate lumen, e.g., similar to the configuration shown in FIG. 14C.

The inner member 330 may be movable between a first or distal position, shown in FIG. 8A, where the outlet 327 is spaced apart from the proximal portion 338, and a second or proximal position, shown in FIG. 8B, where the tapered portion 338 engages the outlet 327 to substantially seal the outlet 327. For example, the actuator may be directed between distal and proximal positions on the handle to open and close the outlet 327. With the outlet 327 open and the inner member 330 in the first position, as shown in FIG. 8A, fluid delivered through the first lumen 326 may exit the outlet 327 into a body lumen or other region adjacent, e.g., proximal to, the distal portion 348, as represented by arrows 95. With the outlet 327 closed and the inner member 330 in the second position, as shown in FIG. 8B, fluid delivered through the first lumen 326 may enter the proximal port(s) 339a of the passage(s) 339 and exit the distal port(s) 339b, e.g., distally beyond the distal portion 348, as represented by arrows 95.

Thus, the inner member 348 may be actuated to selectively deliver fluid on either side of the distal portion 348. During use, the apparatus 310 may be introduced into a body lumen to perform one or more medical procedures, similar to the other embodiments herein. For example, the distal portion 348 may be positioned at a target treatment site, and a treatment element (not shown) on the distal portion 348 may be used to treat the target site. During such treatment, fluid may be delivered proximal or distal to the treatment element, e.g., to monitor use of the treatment element, similar to other embodiments herein.

Figure 9:
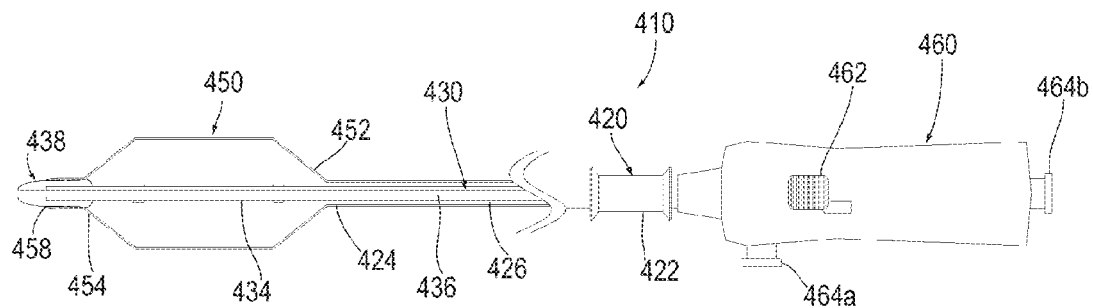
FIG. 9 is a side view of another embodiment of an apparatus including a balloon for treating a body lumen and a valve for selectively delivering fluid from the apparatus.
Figure 10A:
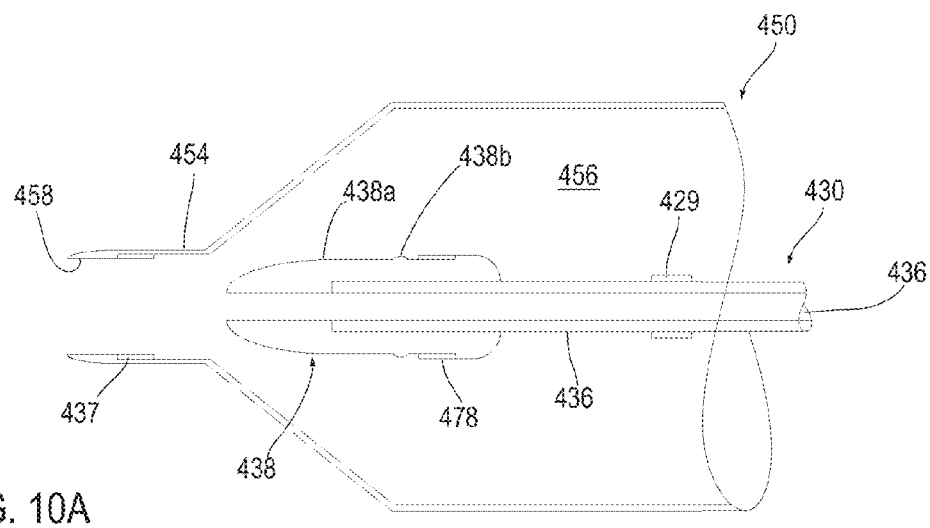
FIGS. 10A and 10B are details of a distal end of the apparatus of FIG. 9, showing the valve in open and closed positions, respectively.
Figure 10B:
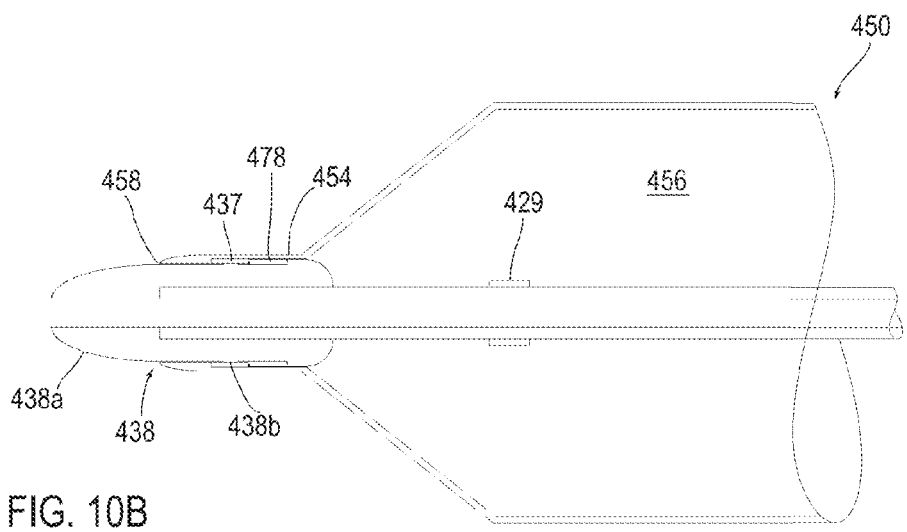

Turning to FIGS. 9-10B, another embodiment of an apparatus 410 is shown for treating a body lumen that includes an outer tubular member 420, an inner member 430, and an expandable balloon 450 carried by the inner and/or outer members 420, 430. Similar to the previous embodiments, the apparatus 410 may be operable in multiple modes, for example, a first mode for delivering fluid into a body lumen (FIG. 10B), and a second mode for expanding the balloon 450 (FIG. 10B), e.g., to remove material, dilate, or otherwise treat a body lumen, deliver a prosthesis, and the like, similar to other embodiments herein.

As best seen in FIG. 9, the outer member 420 includes a proximal end 422, a distal end 424 sized for introduction into a body lumen, and a first lumen 426 extending therebetween. The inner member 430 also includes a proximal end (not shown), a distal end 434, and, optionally, may include a second lumen 436 extending between the proximal and distal ends 434, which may be sized to slidably receive a guide wire or other instrument (not shown) therethrough.

The balloon 450 includes a proximal end 452 coupled to the outer member distal end 424, a distal end 454 including an outlet 458, and an interior 456 communicating with the first lumen 426 and the outlet 458. The distal end 454 of the balloon 450 may be integrally formed with the main wall of the balloon 450 (defining the interior 456), and, optionally, the proximal end 452 of the balloon 450. The balloon 450 may be formed from elastic material, e.g., to provide a compliant or semi-compliant balloon, or from substantially inelastic material, e.g., to provide a non-compliant balloon, similar to other embodiments herein and in the applications incorporated by reference herein.

As best seen in FIGS. 10A and 10B, a distal tip 435 may be integrally formed with, attached to, or otherwise provided on the distal end 454 of the balloon 450, e.g., surrounding or otherwise defining the outlet 458 and/or reinforcing the distal end 454. For example, as shown, the distal tip 435 may include a tapered outer shape, e.g., to provide a substantially atraumatic tip for the balloon 450. In addition, the distal tip 435 includes a stepped-down inner surface, e.g., defining a relatively small diameter distal region 435a and a relatively large diameter proximal region 435b. Optionally, a valve seal liner 437 may be provided within the outlet 458, e.g., in the recess defined by the stepped-down regions 435a, 435b, to further support the outlet 458 and/or distal tip 435, if desired. The valve seal liner 437 may be a separate sleeve attached to the distal tip 435, e.g., by an interference fit, bonding with adhesive, sonic welding, fusing, and the like. For example, the liner sleeve may be formed from a tube or other material having greater radial and/or longitudinal rigidity than the distal tip 454 of the balloon 450. Alternatively, the valve seal liner 437 may be integrally formed with the distal tip 435 and/or distal end 454 of the balloon 450, e.g., with properties of the material modified to enhance support of the distal end 454 and/or outlet 458.

A sealing or valve member 438 may be carried on the inner member distal end 434, e.g., such that the sealing member 438 is movable relative to the balloon 450 as the inner member 430 is moved, e.g., for selectively opening and closing the outlet 458 to provide a valve. Unlike the previous embodiments, the sealing member 438 is disposed within the interior 456 of the balloon 450 such that the sealing member 438 may be spaced apart from the outlet 458 in the proximal or first position to open the outlet 458, and may be seated within the distal end 454 and/or distal tip 435 in the distal or second position to seal the outlet 458.

For example, the sealing member 438 may include a main valve body 438a having a size, e.g., outer diameter, such that the valve body 438a may be slidably received within or through the outlet 458 in the distal position. Optionally, the sealing member 438 may have a tapered shape, e.g., to guide or otherwise facilitate seating the sealing member 438 within the outlet 458 and/or to provide an atraumatic tip when the sealing member 438 is seated in the outlet 458. The sealing member 438 may be formed from flexible material, e.g., which may enhance engagement with the distal end 454 of the balloon 450 and/or the distal tip 435. Optionally, the sealing member 438 may include a substantially atraumatic tip, e.g., a rounded, softened, beveled, or "J" or other curved tip, (not shown), that may extend beyond the distal tip 435, similar to embodiments in the applications incorporated by reference herein.

One or more valve seals, e.g., annular valve seal 438b may be integrally formed on or attached to the valve body 438a, similar to previous embodiments, e.g., to enhance a seal between the sealing member 438 and the distal end 454 of the balloon 450 and/or the distal tip 435. In addition or alternatively, a stop 478 may be provided on the sealing member 438 for limiting distal movement of the inner member 430 relative to the distal end 454 of the balloon 450. As best seen in FIGS. 10A and 10B, the stop 478 may be a band attached around the sealing member 438 proximal to the valve seal 438b.

For example, as shown in FIG. 10A, the inner member 430 may be directed proximally, e.g., until the sealing member 438 is withdrawn entirely into the interior 456 of the balloon 450, thereby opening the outlet 458. Thus, fluid delivered into the first lumen 426 passes through the interior 456 and distal end 454 of the balloon 450 and through the distal tip 435 and outlet 458 into the body lumen beyond the apparatus 410. Alternatively, the inner member 430 may be withdrawn to partially withdraw the sealing member 438 from the outlet 458, e.g., as shown in FIG. 15A, to provide some resistance to flow through the outlet 458 such that the balloon 450 is partially inflated while fluid is delivered from the outlet 458.

Turning to FIG. 10B, the inner member 430 may be directed distally to direct the sealing member 438 into and/or through the distal end 454 of the balloon 450 and/or the distal tip 435 to substantially seal the outlet 458. The sealing member 438 and/or distal end 454, e.g., the valve seal liner 437 and the valve seal 438b, may be sufficiently flexible to contact one another with a relatively high contact pressure, e.g., by deformation of one or both of the valve seal liner 437 and/or the valve seal 438b, to provide a substantially fluid-tight seal with minimal friction. Thus, in this position, fluid delivered into the first lumen 426 of the outer member 420 may remain within the balloon interior 456 to expand the balloon 450.

As shown, the stop 478 and valve seal liner 437 may have substantially flat and/or blunt end surfaces that contact one another, e.g., to prevent further advancement of the inner member 430. The stop 478 and valve seal liner 437 may provide sufficient support to reduce the risk of the distal end 454 of the balloon 450 migrating distally as may otherwise occur as pressurized fluid is delivered into the interior 456 to expand the balloon 450. Optionally, the inner member 430 may be advanced to press the stop 478 against the distal end 454 and/or distal tip 435 and push the distal end 454 of the balloon 450 away from the proximal end (not shown), thereby slightly stretching the balloon 450 and/or enhancing the seal. This configuration may also minimize or otherwise reduce the profile of the balloon 450, e.g., to facilitate introduction into a patient's body. Alternatively, distal advancement of the inner member 430 may be limited, e.g., by an actuator on the proximal end (not shown) of the apparatus 410. Optionally, the valve seal liner 437, distal end 454, distal tip 435, and/or the sealing member 438 may include a lubricious coating or material, such as PTFE, if desired to reduce friction between the components, similar to embodiments in the applications incorporated by reference herein.

With the inner member 430 advanced to close the outlet 458, the sealing member 438 may be received substantially within the distal end 454 of the balloon 450 and/or the distal tip 435. Thus, the sealing member 438 may be disposed substantially entirely beyond the expandable portion of the balloon 450, i.e., outside the interior 456. This configuration may facilitate folding, compressing, or otherwise minimizing a profile of the balloon 450 in its collapsed condition, which may facilitate introduction of the apparatus 410 into a body lumen.

Figure 11:
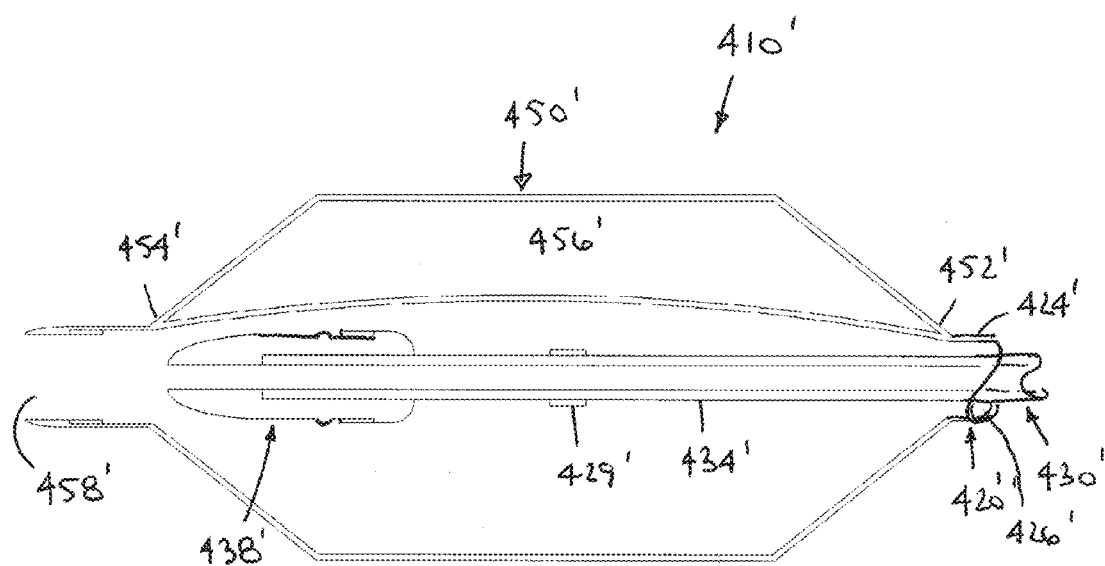
FIG. 11 is a side view of a distal end of an alternative embodiment of the apparatus of FIG. 9, including a tensioning element for biasing the ends of the balloon away from one another.

In an alternative embodiment, shown in FIG. 11, an apparatus 410' may be provided generally similar to the apparatus 410, e.g., including an outer member 420,' an inner member 430' including a sealing member 438,' and a balloon 450' including an outlet 458.' Unlike the previous embodiment, a tensioning element 457' is coupled to the balloon 450,' e.g., a spring or support with opposing ends coupled to proximal and distal ends 452,' 454' of the balloon 450.' The tensioning element 457' may apply a substantially constant tension on the balloon 450' pushing the ends 452,' 454' away from one another. For example, if friction is encountered when the inner member 430' is directed proximally to withdraw the sealing member 438' from the distal end 452' to open the outlet 458,' the tension may prevent the distal end 454' of the balloon 450' from following the sealing member 438' and buckling or otherwise compressing the balloon 450' axially rather than opening the outlet 458.'

Figure 12A:
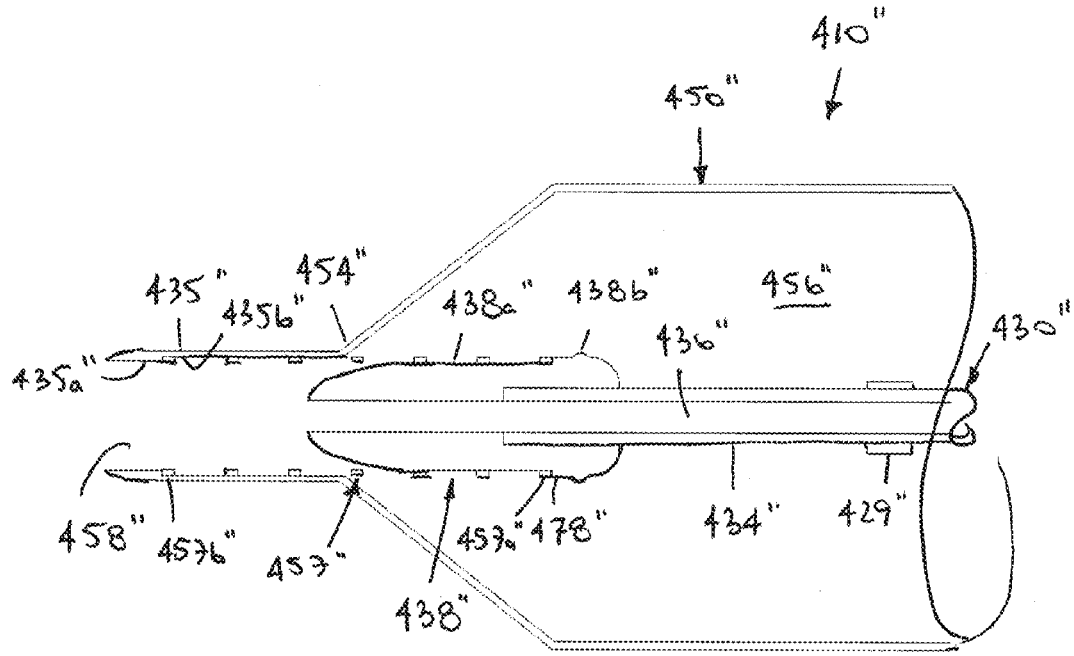
FIGS. 12A and 12B are side views of a distal end of another alternative embodiment of the apparatus of FIG. 9, including a tensioning element for biasing the ends of the balloon away from one another, and showing the valve in open and closed positions, respectively.
Figure 12B:
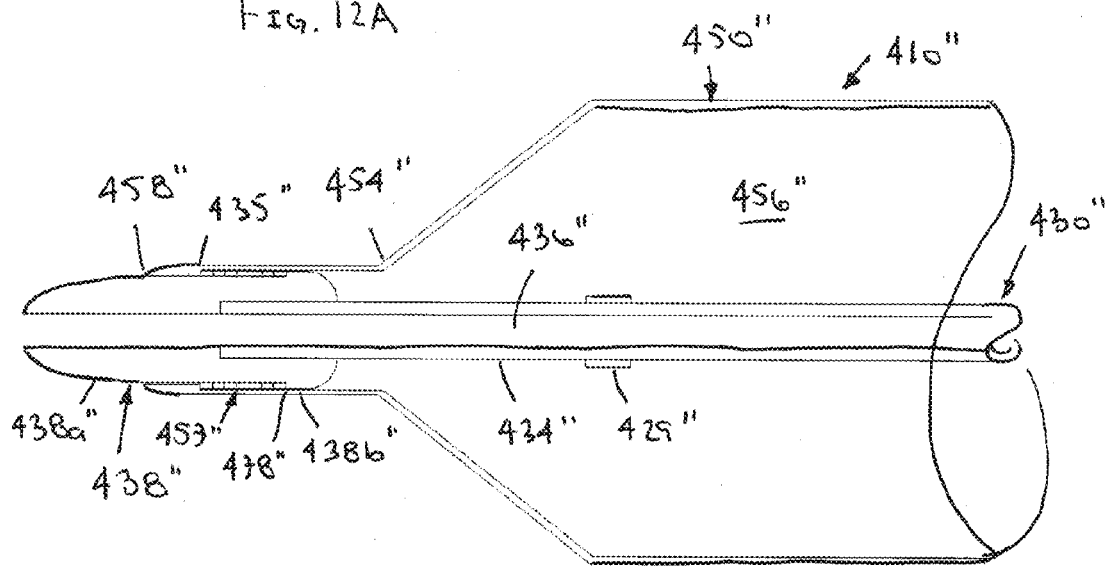

Turning to FIGS. 12A and 12B, another embodiment of an apparatus 410" is shown for treating a body lumen that includes an outer tubular member (not shown), an inner member 430" with a sealing member 438," and an expandable balloon 450" carried by the outer member and inner member 430," generally similar to previous embodiments. Also similar to previous embodiments, the apparatus 410" may be operable in multiple modes, e.g., a first mode for infusing fluid into a body lumen via outlet 458" (FIG. 12A), and a second mode where the outlet 458" is sealed by the sealing member 438" for expanding the balloon 450" (FIG. 12B).

The outer member includes a proximal end, a distal end sized for introduction into a body lumen, and a first lumen extending between the proximal and distal ends (not shown), which may be constructed similar to previous embodiments. The inner member 430" also includes a proximal end (not shown), a distal end 434," and, optionally, a second lumen 436" extending therebetween. The inner member 430" is slidably received within the first lumen of the outer member, e.g., such that an annular space is defined between the outer and inner members 430" for passing one or more fluids therethrough, also similar to previous embodiments.

The balloon 450" includes a proximal end (not shown) coupled to the outer member distal end, a distal end 454" defining the outlet 458," and an interior 456" communicating with the first lumen and the outlet 458." The balloon 450" may be formed from elastic material, e.g., to provide a compliant or semi-compliant balloon, or from substantially inelastic material, e.g., to provide a non-compliant balloon, similar to other embodiments herein. A distal tip 435" may be integrally formed with, attached to, or otherwise provided on the distal end 454" of the balloon 450, e.g., surrounding or otherwise defining the outlet 458" and/or reinforcing the distal end 454." As shown, the distal tip 435" may include a tapered outer shape, e.g., to provide a substantially atraumatic tip for the balloon 450" when the sealing member 328" is fully seated in the outlet 458."

In addition, the distal tip 435" includes a stepped-down inner surface, e.g., defining a relatively small diameter distal region 435a" and a relatively large diameter proximal region 435b." Optionally, a valve seal liner (not shown) may be provided within the outlet 458," e.g., in the recess defined by the stepped-down regions 435a," 435b," similar to the previous embodiment.

A sealing or valve member 438" may be carried on the inner member distal end 434," e.g., within the interior 456" of the balloon 450," such that the sealing member 438" is movable relative to the balloon 450" as the inner member 430" is moved, e.g., for selectively opening and closing the outlet 458" to provide a valve. Similar to previous embodiments, the sealing member 438" may be spaced apart from the outlet 458" in the proximal or first position to open the outlet 458" (FIG. 12A) and may be seated within the distal tip 435" in the distal or second position to seal the outlet 458" (FIG. 12B).

As shown, the sealing member 438" includes a main valve body 438a" having a size, e.g., outer diameter, such that the valve body 438a" may be slidably received within or through the outlet 458," e.g., through the distal region 435a" of the distal tip 435" in the distal position. Optionally, the sealing member 438" may have a tapered shape, e.g., to facilitate seating or other engagement by the sealing member 438" with the distal tip 435" and/or to provide an atraumatic tip when the sealing member 438" is seated within the outlet 458." The sealing member 438" may be formed from flexible material, e.g., which may enhance engagement with the distal tip 435" and/or distal end 454" of the balloon 450."

An annular valve seal 438b" may be integrally formed on or attached to the valve body 438a," similar to previous embodiments, to enhance a seal between the sealing member 438" and the distal tip 435" and/or distal end 454" of the balloon 450." In addition or alternatively, a stop 478" may be provided on the sealing member 438" for limiting distal movement of the inner member 430" relative to the distal end 454" of the balloon 450."

The valve seal 438b" may be sufficiently flexible such that the valve seal 438b" is compressed slightly inwardly when received within the distal end 454" and/or outlet 458," e.g., within the proximal region 435b" of the distal tip 435," to provide a substantially fluid-tight seal without creating substantial friction between the valve seal 438b" and the distal end 454." Alternatively, as shown in FIGS. 13A and 13B, a sealing member 438'" may be provided that includes a valve seal 438b'" that has a relaxed outer diameter that is slightly smaller than the proximal region 435b'" of the distal end 454.'" Thus, the valve seal 438b'" and sealing member 438'" may be freely seated and/or withdrawn from the outlet 458'" and/or distal end 454'" with minimal or no interference and/or friction, as shown in FIG. 13A.

However, in this alternative, the valve seal 438b'" may be formed from relatively soft, flexible material such that, as shown in FIG. 13B, when the inner member 430'" is pushed distally with sufficient force, the valve seal 438b" may compress axially and consequently expand radially, thereby engaging the proximal region 435b'" of the distal tip 435.'" This interference fit may then provide a substantially fluid-tight seal of the outlet 458.'" In addition, as the balloon 450'" is inflated, the pressurization within the interior 456'" may apply a distal force on the sealing member 438'" to further compress the sealing member 438'" and expand the valve seal 438b.'" Once the internal pressure within the balloon 450'" and/or distal force on the inner member 430'" is removed, the valve seal 438b'" may resiliently contract radially, thereby disengaging the proximal region 435b'" and reducing any interference or friction that may otherwise resist withdrawal of the sealing member 438'" from the outlet 458.'"

Returning to FIGS. 12A and 12B, as shown, a tensioning element 457" may be provided for applying tension on the balloon 450" (or other embodiments herein), e.g., to push the distal end 454" distally. As shown, the tensioning element 457" may be a compression spring with a first end 457a" coupled to the stop 478" on the sealing member 438" and a second end 457a" coupled to the distal end 454," e.g., the recess between the stepped-down regions 435a," 435b." The tensioning element 457" may be configured for applying a predetermined, e.g., substantially constant, tension between the inner member 330" and the distal end 454" of the balloon 450," e.g., to apply tension between the proximal and distal ends 452," 454" of the balloon 450" during use of the apparatus 410."

For example, as shown in FIG. 12A, the inner member 430" may be directed to a proximal or first position, e.g., where the sealing member 438" is withdrawn entirely into the interior 456" of the balloon 450," thereby opening the outlet 458." Thus, fluid delivered into the first lumen 426" passes through the interior 456" and distal end 454" of the balloon 450" and through the distal tip 435" and outlet 458" into the body lumen beyond the apparatus 410" without substantial expansion of the balloon 450" (or partial expansion of the balloon 450," similar to the apparatus 410 shown in FIG. 15A and described further below). In the proximal position, the tensioning element 457" may be under slight compression or in a substantially relaxed state, e.g., such that the tensioning element 457" is not stretched or otherwise plastically deformed.

Turning to FIG. 12B, the inner member 430" may be directed to a distal or second position, where the sealing member 438" is advanced into and/or through the distal tip 435" and/or distal end 454" of the balloon 450" to substantially seal the outlet 458." As the inner member 430" is advanced, the tensioning element 457" may be compressed, thereby biasing the distal tip 435" and/or distal end 454" to move distally away from the sealing member 438." In this position, fluid delivered into the first lumen 426" of the outer member 420" may remain within the balloon interior 456" to expand the balloon 450," similar to previous embodiments.

Subsequently, if the inner member 430" and sealing member 438" are again directed proximally to open the outlet 458," the tensioning member 457" may ensure that the distal end 454" and distal tip 435" do not move proximally with the sealing member 438." For example, as explained above, if friction is encountered between the sealing member 438" and distal tip 435" when the inner member 430" is directed proximally to open the outlet 458," the force of the tensioning element 457" may prevent the distal end 454" of the balloon 450" from following the sealing member 438" and potentially buckling or compressing the balloon 450" rather than opening the outlet 458."

During use, any of the apparatus 410-410'" may be used to perform one or more procedures within a body, similar to the other apparatus and methods described elsewhere herein and in the applications incorporated by reference herein. For example, with reference to the apparatus 410 of FIGS. 9-10B, with the sealing member 438 sealing the outlet 458 and the balloon 450 in a contracted condition, the apparatus 410 may be introduced into a patient's body, e.g., into a body lumen, such as a blood vessel (not shown). When desired, the sealing member 438 may be directed to the proximal position to withdraw the sealing member 438 from the distal tip 435 and/or distal end 454, and deliver fluid, such as contrast, dyes, therapeutic agents, and the like, via the outlet 458 into the body lumen, similar to other embodiments herein. Once the balloon 450 is positioned at a desired location, the sealing member 438 may be advanced to the distal position to seal the outlet 458, and the balloon 450 may be expanded within the body lumen, e.g., to remove material, dilate the body lumen, expand a prosthesis (not shown) carried on the balloon 450, deliver agents (also not shown) carried by the balloon 450, and the like, similar to other embodiments herein.

Optionally, as shown in FIG. 15A, during use, the sealing member 438 may be directed to an intermediate position such that the outlet 458 is not fully sealed. Thus, when fluid is introduced through the first lumen 426 of the outer member 420 into the interior 456 of the balloon 450, the balloon 450 may be partially inflated, while fluid also exits the outlet 458. The relative amount of expansion and fluid delivery may be manually adjusted, if desired, e.g., based upon the anatomy and/or intended procedure. For example, the handle may include an indicator (not shown) to identify one or more intermediate positions. In addition, the user may be able to identify an intermediate position based on resistance to fluid being injected, e.g., with increased resistance indicating that the balloon 450 is being inflated.

In an exemplary procedure, it may be desirable to substantially fill a body lumen with radiopaque contrast to facilitate imaging without natural flow within the body lumen washing the contrast away too quickly to obtain a clear image. At least partially inflating the balloon 450 may reduce flow through the body lumen to allow contrast delivered from the outlet 458 to dwell within the body lumen to enhance such imaging. For example, once sufficient fluid is introduced into the body lumen and balloon 450, the sealing member 438 may be advanced to seal the outlet 458 and maintain the balloon 450 in the partially or fully expanded condition for a desired amount of time. After sufficient time has passed, vacuum may be applied to the first lumen 426 to evacuate fluid from the balloon 450 to collapse the balloon 450 and restore normal flow. Alternatively, the sealing member 438 may be withdrawn to open the outlet 458 and allow the balloon 450 to deflate and/or vacuum may be applied to evacuate fluid from the body lumen as well as the balloon 450.

In another exemplary procedure, one or more therapeutic agents, such as thrombus lysing agents or vasodilators, may be delivered into a body lumen via the outlet 458. Causing the balloon 450 to at least partially expand may allow greater residence time of the agent(s) in a target treatment site. As a result, there may be improved effectiveness of the agent(s) and/or smaller volumes may be delivered since natural flow through the body lumen may be temporarily slowed or stopped by the balloon 450.

Figure 17:
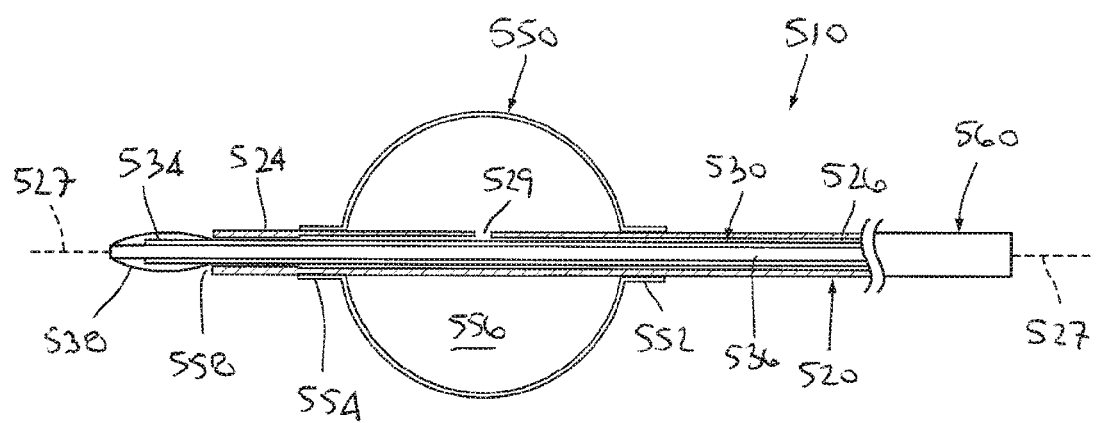
FIG. 17 is a side view of a distal end of yet another exemplary embodiment of an apparatus for treating a body lumen.

Turning to FIG. 17, still another embodiment of an apparatus 510 is shown for treating a body lumen similar to other embodiments herein. As shown, the apparatus 510 includes an outer tubular member 520, an inner member 530, an expandable balloon 550, and a handle 560, which may be constructed similar to previous embodiments and the embodiments in the applications incorporated by reference herein.

The outer member 520 includes a proximal end (not shown), a distal end 524 sized for introduction into a body lumen, and a first lumen 526 extending along a central longitudinal axis 527 therebetween. The inner member 530 also includes a proximal end (not shown), a distal end 534, and, optionally, a second lumen 536, e.g., sized to slidably receive a guidewire or other instrument (not shown) therethrough. The inner member 530 may be slidably received within the first lumen 526 of the outer member 520, e.g., such that an annular space is defined between the outer and inner members 520, 530 for passing one or more fluids therethrough, also similar to previous embodiments. One or more sealing members, e.g., a nosecone 538, may be provided on the distal end 534 of the inner member 530 to provide a valve, also similar to previous embodiments.

Unlike previous embodiments, the balloon 550 includes proximal and distal ends 552, 554 that are both attached or otherwise coupled to the outer member 520. The outer member 520 includes one or more openings 529 in the distal end 524 such that an interior 556 communicates with the first lumen 526 via the opening(s) 529. The distal end 534 of the inner member 530 may extend through the distal end 524 of the outer member 520, e.g., beyond an outlet 558 in the outer member 520 such that the outlet 558 defines an annular passage between the outer and inner members 520, 530. Alternatively, the distal end of the balloon may be attached to the inner member or the distal end of the balloon may include an outlet end that surrounds the inner member, e.g., similar to embodiments disclosed elsewhere herein and in the applications incorporated by reference herein.

With continued reference to FIG. 17, the handle 560 may be attached to or otherwise provided on the proximal end of the outer member 520, e.g., for manipulating the outer member 520 and/or the entire apparatus 510. Similar to previous embodiments and embodiments in the applications incorporated by reference herein, the handle 560 may include an actuator (not shown) for operating the apparatus 510 in multiple modes, e.g., a first mode for dilating an obstruction within a body lumen, and a second mode for infusing fluid into a body lumen. For example, the actuator may be movable to direct the inner member 530 relative to the outer member 520 between a first or proximal position where the nosecone 538 may be partially received in or otherwise engage the distal end 524 of the outer member 520 to substantially seal the outlet 558 and a second or distal position where the nosecone 538 is spaced away from the outer member 520 to open the outlet 558, similar to previous embodiments.

With the nosecone 538 sealing the outlet 558, any fluid introduced into the first lumen 526 enters the interior 556 of the balloon 550, thereby expanding the balloon 550. Unlike previous embodiments, because both the proximal and distal ends 552, 554 of the balloon 550 are attached to the outer member 520, the length of the balloon 550 may remain substantially constant during expansion and/or collapse. With the nosecone 538 directed away from the outer member 520 to open the outlet 558, the balloon 550 may remain collapsed and any fluid introduced through the first lumen 526 may exit the outlet 558 into a body lumen within which the apparatus 510 is introduced.

As shown, the inner member 530 may be integrally incorporated into the apparatus 510, similar to previous embodiments. Alternatively, the inner member 530 may be decoupled or independent from the other components of the apparatus 510. For example, in one embodiment, the inner member 530 may be introduceable into a patient's body independently from the outer member 520, e.g., over a guidewire or instead of a guidewire. Once the distal end 534 is positioned at a desired location within the patient's body, the rest of the apparatus 510, i.e., the outer member 520 with the balloon 550 collapsed may be advanced over the inner member 530 to the desired location.

For example, the proximal end of the inner member 530 extending from the patient's body may be backloaded through the outlet 558, and the outer member 520 advanced until the proximal end of the inner member 530 is received in or extends from the handle 560. The relative length of the outer and inner members 520, 530 may be such that the outlet 558 is disposed adjacent the nosecone 538 when the proximal end of the inner member 530 is received in or extends from the handle 560.

If desired, the handle 560 may include a coupler (not shown) that may be activated to engage the inner member 530 to a push button, thumb control, or other actuator (not shown) on the handle 560 once the outer member 520 is advanced sufficiently over the inner member 530. Thus, subsequently, the actuator may be activated to direct the inner member 530 and nosecone 538 axially relative to the outer member 520 to seal or open the outlet 558. It will be appreciated that other embodiments described elsewhere herein may be decoupled in this manner, i.e., provided with the inner member independent from the outer member and/or other components of the apparatus.

Optionally, an independent inner member 530 may include one or more markers or other visual indicators (not shown) that may provide confirmation to a user that the outer member 520 has been advanced sufficiently to place the outlet 558 adjacent the nosecone 538. For example, a marker may be provided on the proximal end of the inner member 530 that may be visible when the proximal end of the inner member 530 extends from the handle 560, thereby providing a visual indication that the nosecone 538 is sealing or adjacent the outlet 558. In addition or alternatively, the outer member 520 may be advanced until the distal end 524 contacts or engages the nosecone 538, which may provide tactile feedback that the nosecone 538 may be used to seal or open the outlet 558.

With the outer member 520 advanced over the inner member 530, the outlet 558 may be opened and fluid delivered into the desired location, e.g., contrast to facilitate imaging the desired location, or one or more diagnostic and/or therapeutic agents. If desired to expand the balloon 550, the nosecone 538 may be directed proximally to seal the outlet 558, and fluid delivered to inflate the balloon 550, e.g., to dilate a stenosis or other lesion at the desired location, similar to methods described elsewhere herein. After treating the desired location, the apparatus 510 may be directed to another location or removed from the patient's body. For example, the outer and inner members 520, 530 may be removed together or the outer member 520 may be removed first (e.g., after decoupling the outer member 520 from the inner member 530 if coupled together after advancing the outer member 520 over the inner member 530).

Figure 18C:
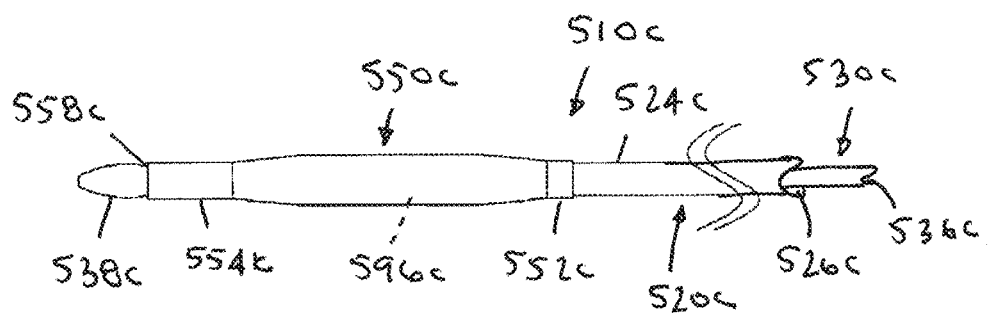

In alternative embodiments, one or more treatment elements may be provided in addition to or instead of the balloon 550. For example, as shown in FIG. 18A, an apparatus 510a may be provided that is generally similar to apparatus 510, except that a prosthesis 596a is provided on the distal end 524a. In an exemplary embodiment, the prosthesis 596a may be a stent that may be crimped or otherwise loaded over the balloon 550a. Once the distal end 524a of the apparatus 510a is positioned within a target treatment site, e.g., after opening the outlet 558a to deliver contrast and facilitate positioning the stent 596a, the outlet 558a may be sealed with the nosecone 538a, and the balloon 550a inflated to expand the stent 596a within the target treatment site, e.g., to dilate and support an obstructed region within a blood vessel. Alternatively, other prostheses may be loaded on the apparatus 510a, such as a stent-graft, a prosthetic valve, and the like, similar to other embodiments herein.

Turning to FIG. 18B, another embodiment of an apparatus 510b is shown that includes a plurality of treatment elements, namely a plurality of electrodes or other conductive elements 596b on the balloon 550b. The elements 596b may be attached to or embedded in the balloon wall 550b in a desired pattern, e.g., a plurality of longitudinal elements spaced apart from one another about a circumference of the balloon 550b, as shown. The elements 596b may be coupled to an energy source, e.g., a radiofrequency generator coupled to a handle (not shown) on the proximal end of the apparatus 510b. For example, a plurality of wires or other conductors (not shown) may extend through the outer member 520b from the elements 596b to a connector on the handle (not shown) to which the generator may be connected.

During use, once the distal end 524b of the apparatus 510b has been positioned within a target treatment site, e.g., within a blood vessel, heart chamber, and the like (not shown), the balloon 550b may be inflated to expand the elements 596b, e.g., to press them against the wall of the body lumen. The generator may then be activated to deliver energy into the wall via the elements 596b, to ablate, heat, or otherwise treat tissue surrounding the body lumen. Similar to previous embodiments, the outlet 558b may be selectively opened and closed during the procedure, e.g., before or after delivering the energy, to facilitate imaging, or otherwise monitor or enhance treatment.

Turning to 18C, yet another embodiment of an apparatus 510c is shown that includes one or more cryogenic treatment elements 596c carried by the balloon 550c and/or the distal end 524c of the apparatus 510c. In an exemplary embodiment, the cryogenic element(s) may include a cooling apparatus within the balloon 550c powered by compressed gas having thermodynamic properties that cause cooling upon expansion of the gas within the interior of the balloon 550c.

During use, once the distal end 524c of the apparatus 510c has been positioned within a target treatment site, e.g., within a blood vessel, heart chamber, and the like (not shown), the balloon 550c may be inflated, e.g., to press the balloon 550c against the wall of the body lumen. Cooling gas may then be released within the interior of the balloon 550c to cool surrounding tissues to freeze, modify, or otherwise treat tissue surrounding the body lumen, e.g., to reduce the risk of restenosis within a blood vessel. Similar to previous embodiments, the outlet 558c may be selectively opened and closed during the procedure, e.g., before or after delivering the cooling gas, to facilitate imaging, or otherwise monitor or enhance treatment.

Turning to FIGS. 19A and 19B, another embodiment of an apparatus 610 is shown that includes an outer tubular member 620, an inner member 630, and an expandable balloon 650, which may be constructed similar to previous embodiments and the embodiments in the applications incorporated by reference herein. For example, the outer member 620 may include a proximal end (not shown), a distal end 624 sized for introduction into a body lumen, and a first lumen 626 extending therebetween.

The inner member 630 also includes a proximal end (not shown), a distal end 634, and a second lumen 636 extending therebetween. Unlike the previous embodiments, the second lumen 636 may be sized for receiving one or more instruments therethrough, e.g., one or more catheters, sheaths, or other devices (not shown), which may be substantially larger than a guidewire. For example, the second lumen 636 may have a diameter between about one and four millimeters (1-4 mm). Thus, the apparatus 610 may provide a guide catheter or guide sheath that may be introduced into a body lumen and through which one or more other devices may be introduced to perform a procedure. Optionally, a dilator (not shown) may be provided within the second lumen 636, e.g., to support the apparatus 610 and/or to provide a transition or atraumatic tip for the apparatus 610.

Similar to previous embodiments, the inner member 630 may be slidably received within the first lumen 626 of the outer member 620, e.g., such that an annular space is defined between the outer and inner members 620, 630 for passing one or more fluids therethrough. One or more sealing members, e.g., a nosecone 638, may be provided on the distal end 634 of the inner member 630 to provide a valve, also similar to previous embodiments.

The balloon 650 includes proximal and distal ends 652, 654 that are both attached or otherwise coupled to the outer member 620, and the outer member 620 may include one or more openings (not shown) in the distal end 624 such that an interior of the balloon 650 communicates with the first lumen 626 via the opening(s). The distal end 634 of the inner member 630 may extend through the distal end 624 of the outer member 620, e.g., beyond an outlet 658 in the outer member 620 such that the outlet 658 defines an annular passage between the outer and inner members 620, 630. Alternatively, the distal end 654 of the balloon 650 may be attached to the inner member 630 or the distal end 654 of the balloon 650 may include an outlet end that surrounds the inner member, e.g., similar to embodiments disclosed elsewhere herein and in the applications incorporated by reference herein.

With the nosecone 638 sealing the outlet 658, any fluid introduced into the first lumen 626 enters the interior of the balloon 650, thereby expanding the balloon 650. With the nosecone 638 directed away from the outer member 620 to open the outlet 658, the balloon 650 may remain collapsed and any fluid introduced through the first lumen 626 may exit the outlet 658 into a body lumen within which the apparatus 610 is introduced. Thus, the apparatus 610 may provide a guide or access sheath that includes a valve adjacent the balloon 650, which may be selectively opened and closed to deliver fluid when the second lumen 636 is used for other purposes.

Turning to FIGS. 20A and 20B, still another embodiment of an apparatus 710 is shown that includes a catheter or other elongate member 720 including proximal and distal ends 722, 724 and a balloon 750 carried on the distal end 724. Optionally, the apparatus 710 may include an inner member and/or valve (not shown), similar to previous embodiments and embodiments in the applications incorporated by reference herein.

In addition, the apparatus 710 includes a handle 750 coupled to or otherwise on the proximal end 722 that includes an integrated inflation device. Previous embodiments generally include a handle with a port to which an external inflation device, such as a syringe and the like (not shown) may be coupled. Thus, unlike the previous embodiments, the apparatus 710 includes an inflation device incorporated directly into the handle 750.

Generally, the inflation device includes a barrel or housing 752 and a piston 754 slidably received in the barrel 752 such that a fluid-tight seal is provided between the piston 754 and barrel 752. The handle 750 may include a fixed gripping surface 756 coupled to the barrel 752 and a movable gripping surface 758 coupled to the piston 754. A pressure gauge 766 may be attached to the barrel 752 to provide an indicator of the pressure of fluid within the barrel 752. A filling port 768 is attached to or extends from the barrel 752, e.g., including a valve that may be selectively opened and closed, to allow fluids (e.g., liquids or gases) to be delivered into or removed from the barrel 752. For example, when the balloon 750 is to be inflated, the valve may be closed to provide a fixed volume of fluid for delivery into the balloon 750.

In exemplary embodiments, the valve may include a control, e.g., a button, lever, stopcock, and the like (not shown), that may be manually opened and closed by the user, or the valve may be automatically opened and closed, e.g., when a luer fitting or other connector (not shown) is connected to or disconnected from the filling port 768, e.g., a luer-activated valve. The piston 754 includes one or more helical threads 760 on its exterior surface that may be engaged with a split nut assembly or other actuator 764. The assembly 764 may include a button 762 that, when pushed or otherwise activated, disengages the split nut threads from the piston threads 760.

During use, the distal end 724 of the catheter 720 may introduced into a body lumen, e.g., similar to other embodiments herein. To inflate the balloon 750, the piston 754 may be advanced relative to the barrel 752. For example, the user may hold the fixed gripping surface 756 with one hand and the movable gripping surface 758 with the other. The button 762 on the split nut assembly 764 may be depressed to disengage the threads 760, and the piston 754 may be advanced into the barrel 752 to inject fluid through the catheter 720 into the balloon 750. The button 762 may then be released, and the threads 760 may automatically reengage. Thereafter, if it is desired to advance or retract the piston 754, the movable gripping surface 758 may be rotated and the split nut assembly 762 may slide along the threads 760, e.g., to advance the piston 754 further into the barrel 752. In this manner, a higher force (and resulting pressure) may be applied to the balloon 750 than by manually advancing the piston 754 with the threads 760 disengaged.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for treating a body lumen of a patient, the method comprising:
    receiving an apparatus comprising:
        an outer member including a first lumen extending between a proximal end and an outlet in a distal end of the outer member,
        an inner member slidable within the first lumen, the inner member including a distal portion extending beyond the outlet of the outer member, the inner member comprising a second lumen,
        a treatment element on the distal portion, and
        a sealing member at least partially proximal to the treatment element on the distal portion, the sealing member being in direct contact with the treatment element, the sealing member having one or more passages in fluid communication with an interior of the treatment element, and the sealing member being sized to at least partially enter the first lumen of the outer member such that the sealing member may substantially seal the outlet of the outer member;
    introducing the distal end of the outer member into the body lumen with the inner member in a proximal position such that the sealing member substantially seals the outlet of the outer member;
    actuating a proximal end of the apparatus to slide the inner member to a distal position, such that the sealing member is directed away from the outlet of the outer member;
    delivering fluid through the first lumen such that some of the fluid exits through the outlet of the outer member into the body lumen and some of the fluid is delivered through the one or more passages in the sealing member directly into the treatment element; and
    performing a procedure within the body lumen using the treatment element,
    wherein the sealing member is configured to slide axially to partially obstruct the outlet of the outer member.

2. The method of claim 1, wherein the treatment element comprises a balloon, the method further comprising:
    directing the inner member towards the proximal position such that the sealing member substantially seals the outlet and the one or more passages in the sealing member communicate between the first lumen and an interior of the balloon; and
    delivering the fluid through the first lumen with the outlet substantially sealed, such that the fluid is delivered through the one or more passages into the interior of the balloon to expand the balloon within the body lumen.

3. The method of claim 2, further comprising:
    directing the balloon to an expanded helical shape within the body lumen; and directing the balloon along a wall of the body lumen in the expanded helical shape to remove material from the wall of the body lumen.

4. The method of claim 2, wherein the treatment element further comprises a prosthesis carried on the distal portion over the balloon, and wherein the prosthesis is expanded within the body lumen when the balloon is expanded.

5. The method of claim 4, wherein the prosthesis comprises at least one of a stent, a stent-graft, and a prosthetic valve.

6. The method of claim 2, wherein the balloon is expanded until the balloon contacts a wall of the body lumen, the method further comprising delivering energy via the balloon to tissue adjacent the wall of the body lumen.

7. The method of claim 2, wherein the balloon is expanded until the balloon contacts a wall of the body lumen, thereby delivering one or more agents carried by the balloon to tissue adjacent the wall of the body lumen.

8. The method of claim 2, wherein the treatment element comprises a carrier on the balloon comprising one or more diagnostic or therapeutic agents, and wherein the carrier is expanded within the body lumen when the balloon is expanded.

9. The method of claim 1, wherein the treatment element comprises a balloon, the method further comprising sliding the inner member towards the proximal position such that the sealing member partially obstructs the outlet of the outer member.

10. The method of claim 9, wherein the apparatus further comprises an actuator on the proximal end of the apparatus, the method further comprising manipulating the actuator to adjust the amount of fluid that exits the outlet of the outer member and is delivered into the interior of the balloon.

11. The method of claim 9, further comprising sliding the inner member towards the proximal position such that the sealing member substantially seals the outlet of the outer member with the balloon partially expanded, thereby reducing normal flow within the balloon.

12. The method of claim 11, further comprising evacuating fluid from the partially expanded balloon through the first lumen to collapse the balloon and allow normal flow to resume within the balloon.

13. The method of claim 11, wherein the fluid comprises a contrast agent, and wherein the balloon is partially expanded for a desired time to reduce washout of the contrast agent by normal flow through the body lumen while the body lumen is imaged.

14. The method of claim 11, wherein the fluid comprises one or more therapeutic agents, and wherein the balloon is partially expanded for a desired time to reduce washout of the one or more therapeutic agents by normal flow through the body lumen to enhance treatment of the body lumen by the one or more therapeutic agents.

15. The method of claim 1, wherein the apparatus further comprises a tensioning element coupled between the inner and outer members, the tensioning element biasing the inner member proximally to enhance the sealing member sealing the outlet of the outer member in the proximal position.

16. The method of claim 1, further comprising aspirating the fluid from the body lumen into the outlet of the outer member and through the first lumen.

17. The method of claim 1, wherein a proximal end of the treatment element overlaps with a distal end of the sealing member.

18. A method for treating a body lumen of a patient, the method comprising:
receiving a balloon apparatus comprising:
an outer member including a first lumen extending between a proximal end and an outlet in a distal end of the outer member,
an inner member slidable within the first lumen, the inner member comprising a second lumen,
a balloon attached to a distal end of the inner member distally beyond the distal end of the outer member, and
a sealing member on the inner member at least partially proximal to the balloon, the sealing member being in direct contact with the balloon, the sealing member having one or more passages in fluid communication with an interior of the balloon, and the sealing member being sized to at least partially enter the first lumen of the outer member such that the sealing member may substantially seal the outlet of the outer member;
introducing the distal end of the outer member into the body lumen with the balloon in a contracted condition and the inner member in a proximal position such that the sealing member substantially seals the outlet of the outer member;
actuating a proximal end of the apparatus to slide the inner member to a distal position, such that the sealing member is directed away from the outlet of the outer member;
delivering fluid through the first lumen such that some of the fluid exits through the outlet of the outer member into the body lumen and some of the fluid is delivered through the one or more passages in the sealing member directly into the interior of the balloon;
sliding the inner member towards the proximal position to substantially seal the outlet of the outer member with the sealing member such that the one or more passages in the sealing member communicate directly between the first lumen and the interior of the balloon; and
delivering the fluid through the first lumen with the outlet substantially sealed, thereby delivering fluid through the one or more passages of the sealing member into the interior of the balloon to expand the balloon from the contracted condition to an enlarged condition,
wherein the sealing member is configured to slide axially to partially obstruct the outlet of the outer member.

19. The method of claim 18, wherein the apparatus further comprises a tensioning element coupled between the inner and outer members, the tensioning element biasing the inner member proximally to enhance the sealing member sealing the outlet of the outer member in the proximal position.

20. The method of claim 18, further comprising:
directing the balloon to an expanded helical shape within the body lumen; and
directing the balloon along a wall of the body lumen in the expanded helical shape to remove material from the wall of the body lumen.

21. The method of claim 18, wherein the balloon further comprises a prosthesis in the contracted condition, and wherein the balloon expands the prosthesis within the body lumen when the balloon is expanded to the enlarged condition.

22. The method of claim 21, wherein the prosthesis comprises at least one of a stent, a stent-graft, and a prosthetic valve.

23. The method of claim 18, further comprising aspirating the fluid from the body lumen into the outlet of the outer member and through the first lumen.

24. The method of claim 18, wherein a proximal end of the balloon overlaps with a distal end of the sealing member.

* * * * *